United States Patent [19]
Bandman et al.

[11] Patent Number: 5,817,482
[45] Date of Patent: Oct. 6, 1998

[54] DISEASE RELATED NUCLEOTIDE KINASES

[75] Inventors: Olga Bandman; Jennifer L. Hillman; Phillip R. Hawkins, all of Mountain View; Karl J. Guegler, Menlo Park; Neil C. Corley, Mountain View, all of Calif.

[73] Assignee: Incyte Pharmaceuticals, Inc., Palo Alto, Calif.

[21] Appl. No.: 879,561

[22] Filed: Jun. 20, 1997

[51] Int. Cl.$^6$ ...................................................... C12N 15/00
[52] U.S. Cl. .................. 435/69.1; 435/252.3; 435/320.1; 435/194; 435/6; 536/23.1; 536/23.5; 536/24.31; 536/24.33; 530/350
[58] Field of Search ................................ 435/69.1, 252.3, 435/320.1, 6, 194; 536/23.1, 23.5, 24.31, 24.33; 530/350

[56] References Cited

PUBLICATIONS

Chottiner, E.G., et al., "Cloning and expression of human deoxycytidine kinase cDNA", *Proc. Natl. Acad. Sci. USA*, 88: 1531–1535 (1991). (GI 181510).

Zeleznikar, R.J., et al., "Adenylate kinase–catalyzed phosphoryl transfer couples ATP utilization with its generation by glycolysis in intact muscle", *J. Biol. Chem.*, 270: 7311–7319 (1995).

Matsuura, S., et al., "Human Adenylate Kinase Deficiency Associated with Hemolytic Anemia", *The Journal of Biological Chemistry*, 264: 10148–10155 (1989). (GI 178322).

Bos, J.L., "ras oncogenes in human cancer: a review", *Cancer Res*, 49: 4682–4689 (1989).

Li, H., et al., "The Isolation and Characterization of cDNA Encoding the Mouse Bifunctional ATP Sulfurylase–Adenosine 5'–Phosphosulfate Kinase", *The Journal of Biological Chemistry*, 270(49): 29453–29459 (1995). (GI 1109676).

Miller, W.H., et al., "Phosphorylation of acyclovir (acycloguanosine) monophosphate by GMP kinase" *J. Biol. Chem.*, 255: 7204–7207 (1980).

Stenberg, K., et al., "Metabolism and mode of action of (R)–9–(3,4–dihydroxybutyl)guanine in herpes simplex virus–infected vero cells", *J. Biol. Chem*, 261: 2134–2139 (1986).

Wang, L., et al., "Cloning and expression on human mitochondrial deoxyguanosine kinase cDNA", *FEBS Letters*, 390:39–43 (1996). (GI 1480198).

Rosenthal, E., et al., "A multifunctional *Urechis caupo* protein, PAPS synthetase, has both ATP sulfurylase and APS kinase activities", *Gene*, 165:243–248 (1995). (GI 705385).

Suminami, Y., et al., "Structure and Complete Nucleotide Sequence of the Gene Encoding Chicken Cytosolic Adenylate Kinase", *J. Biochem*, 103: 611–617 (1988). (GI 222786).

*Primary Examiner*—Robert A. Wax
*Assistant Examiner*—Enrique D. Longton
*Attorney, Agent, or Firm*—Sheela Mohan-Peterson; Lucy J. Billings; Incyte Pharmaceuticals, Inc.

[57] ABSTRACT

The invention provides human nucleotide kinases and polynucleotides which identify and encode DRNK. The invention also provides expression vectors, host cells, agonists, antibodies and antagonists. The invention also provides methods for treating disorders associated with expression of DRNK.

11 Claims, 19 Drawing Sheets

FIGURE 1A

```
5' NTG CCC GTT AGG CCC CGT TAA CGC CTC TCC CTA AGT CGG CTT CGA GCA CCC TTC
                 9          18          27          36          45          54

AGT TCC ATG GCC AAG AGC CCA CTC GAG GGC GTT TCC TCC AGA GGC CTG CAC
                63          72          81          90          99         108
            M   A   K   S   P   L   E   G   V   S   S   R   G   L   H

GCG GGG CGC GGG CCC CGA AGG CTC TCC ATC GAA AAC ATT GCT GTG GGA AAG
               117         126         135         144         153         162
    A   G   R   G   P   R   L   S   I   E   N   I   A   V   G   K

TCC ACG TTT GTG AAG TTA CTC ACG AAA ACT TAC CCA GAA TGG CAC GTA GCT ACA
               171         180         189         198         207         216
    S   T   F   V   K   L   L   T   K   T   Y   P   E   W   H   V   A   T

GAA CCT GTA GCA ACA TGG CAG AAT ATC CAG GCT GCT GGC ACC CAA AAA GCC TGC
               225         234         243         252         261         270
    E   P   V   A   T   W   Q   N   I   Q   A   A   G   T   Q   K   A   C

ACT GCC CAA AGT CTT GGA AAC TTG CTG GAT ATG TAC CGG GAG CCA GCA CGA
               279         288         297         306         315         324
    T   A   Q   S   L   G   N   L   L   D   M   M   Y   R   E   P   A   R
```

```
        333           342           351           360           369           378
    TGG TCC TAC ACA TTC CAG ACA TTT TCC TTT TTG AGC CGC CTG AAA GTA CAG CTG
     W   S   Y   T   F   Q   T   F   S   F   L   S   R   L   K   V   Q   L 387           396           405           414           423           432
    GAG CCC TTC CCT GAG AAA CTC TTA CAG GCC AGG AAG CCA GTA CAG ATC TTT GAG
     E   P   F   P   E   K   L   L   Q   A   R   K   P   V   Q   I   F   E 441           450           459           468           477           486
    AGG TCT GTG TAC AGT GAC AGG TAT ATC TTT GCA AAG AAT CTT TTT GAA AAT GGT
     R   S   V   Y   S   D   R   Y   I   F   A   K   N   L   F   E   N   G 495           504           513           522           531           540
    TCC CTC AGT GAC ATC TCG AGT GGC ATA TCT ATC AGG ACT GGC ATT CTT TTC TCC
     S   L   S   D   I   S   S   G   I   S   I   R   T   G   I   L   F   S 549           558           567           576           585           594
    TGT GGG AGT TTG CCA GCC GGA TCA CAT TAC ATG GCT TCA TCT ACC TCC AGG CTT
     C   G   S   L   P   A   G   S   H   Y   M   A   S   S   T   S   R   L 603           612           621           630           639           648
    CTC CCC AGG TTT GTT TTG AAG AAA CTG TAC CAA AGG GCC AGG GAG GAG GAG AAA
     L   P   R   F   V   L   K   K   L   Y   Q   R   A   R   E   E   E   K
```

FIGURE 1B

```
     657                666                 675                 684                 693                 702
GGA  ATT GAG CTG GCC   TAT CTA GAG CAG CTG  CAT GGC CAA CAC GAA GCC TGG CTT
 G    I   E   L   A     Y   L   E   Q   L    H   G   Q   H   E   A   W   L 711                720                 729                 738                 747                 756
ATT  CAC AAG ACA ACG   AAG CTC CAC TTT GAG  GCT CTG ATG AAC ATT CCA GTG CTG
 I    H   K   T   T     K   L   H   F   E    A   L   M   N   I   P   V   L 765                774                 783                 792                 801                 810
GTG  TTG GAT GTC AAT   GAT GAT TTT TCT GAG  GAA GTA ACC AAA CAA GAA GAC CTC
 V    L   D   V   N     D   D   F   S   E    E   V   T   K   Q   E   D   L 819                828                 837                 846                 855                 864
ATG  AGA GAG GTA AAC   ACC TTT GTA AAG AAT  CTG TAA CCA ATA TGA TGT TCA
 M    R   E   V   N     T   F   V   K   N    L 873                882                 891                 900                 909                 918
GGC  TGT GAT CTG GGC   TCC CTG ACT TTC TGA  AGC TAG AAA AAT GTT GTG TCT CCC 927                936                 945                 954
AAC  CAN CTT TCC ATC   CCC AGC CCC TCT CAT  CCC TGG AGC A 3'
```

```
                  9          18          27          36          45          54
5' NCA GAG AAC  CCC GGC TGC  TCA GCG CGC  TCC GCG ATC  CCC GGG AGC 63          72          81          90          99         108
   CTG TGC AAG  AAA GTC AAG  CTG AGC AAT  GCG AAT AAC  GCG CAG AAC  TGG GGA ATG
    L   C   K    K   V   K    L   S   N    A   N   N    A   Q   N    W   G   M 117         126         135         144         153         162
   GCA ACC AAT  GTC ACC TAC  CAA GCC CAT  CAT GTC AGC  AGG AAC AAG  AGA GGT CAG
    A   T   N    V   T   Y    Q   A   H    H   V   S    R   N   K    R   G   Q 171         180         189         198         207         216
   GTG GTG GGG  ACC AGA GGT  GGC TTT CGT  GGT TGC GGT  GAC ATG GCC  TTG ACA GGC TTG
    V   V   G    T   R   G    G   F   R    G   C   G    D   M   A    L   T   G   L 225         234         243         252         261         270
   TCT GGA GCG  GGA AAG ACT  ACT GTG AGC  ATG GCC TTG  GAG GAG TAC  CTG GTT TGT
    S   G   A    G   K   T    T   V   S    M   A   L    E   E   Y    L   V   C 279         288         297         306         315         324
   CAT GGT ATT  CCA TGC TAC  ACT CTG GAT  GGT GAC AAT  ATT CGT CAA  GGT CTC AAT
    H   G   I    P   C   Y    T   L   D    G   D   N    I   R   Q    G   L   N 333         342         351         360         369         378
   AAA AAT CTT  GGC TTT AGT  CCT GAA GAC  AGA GAA GAG  AAT GTT CGA  CGC ATC GCA
    K   N   L    G   F   S    P   E   D    R   E   E    N   V   R    R   I   A
```

```
                                          387                396                405                414                423                432
                                          GAA GTT GCT        AAA CTG TTT        GCA GAT GCT        GGC TTA GTG        TGC ATC ACA        AGT TTC ATA
                                          E   V   A          K   L   F          A   D   A          G   L   V          C   I   T          S   F   I 441                450                459                468                477                486
                                          TCA CCT TAC        ACT CAG GAT        CGC AAC GCA        AGG CAA ATT        CAT GAA GGT        GCA AGT
                                          S   P   Y          T   Q   D          R   N   A          R   Q   I          H   E   G          A   S 495                504                513                522                531                540
                                          TTA CCG TTT        GAA TTT GTA        TTT GTT GAT        GCT CCT CTG        CAT GTT TGT        GAA CAG AGG
                                          L   P   F          E   F   V          F   V   D          A   P   L          H   V   C          E   Q   R 549                558                567                576                585                594
                                          GAT GTC AAA        GGA CTC TAC        AAA AAA TAC        GAA ATT CAT        GAA GGA GAA ATT   AAA GGT TTC ACT
                                          D   V   K          G   L   Y          K   K   Y          E   I   H          E   G   E   I      K   G   F   T 603                612                621                630                639                648
                                          GGG ATC GAT        TCT GAA TAT        CCA GAG AAG        GCC CCT GAG        TTG GTG CTT        AAA GTT ACA
                                          G   I   D          S   E   Y          P   E   K          A   P   E          L   V   L          K   V   T 657                666                675                684                693                702
                                          GAC TCC TGT        GAT AAT GAC        TGT GTC CAG        CAA GTT GAA        CTT GAA CTA        CAG AAA GAA
                                          D   S   C          D   N   D          C   V   Q          Q   V   E          L   E   L          Q   K   E 711                720                729                738                747                756
                                          CGG GAT ATT        GTA CCT GTG        GAT GCA TCT        TAT GAA GTA        AAA GAA CTA        TAT GTG CCA
                                          R   D   I          V   P   V          D   A   S          Y   E   V          K   E   L          Y   V   P
```

FIGURE 2B

```
     765             774             783             792         801             810
GAA AAT CTT CAT TTG GCA AAA ACA GAT GCG GAA ACA TTA CCA GCA CTG AAA
 E   N   L   H   L   A   K   T   D   A   E   T   L   P   A   L   K 819             828             837             846         855             864
ATT AAT AAA GTG GAT ATG CAG TGG GTG CAG GTT TTG GCA GAA GGT TGG GCA ACC
 I   N   K   V   D   M   Q   W   V   Q   V   L   A   E   G   W   A   T 873             882             891             900         909             918
CCA TTG AAT GGC TTT ATG AGA GAG TAC TTG CAG TGC CTT CAT TTT GAT
 P   L   N   G   F   M   R   E   Y   L   Q   C   L   H   F   D 927             936             945             954         963             972
TGT CTT CTG GAT GGA GGT GTC ATT AAC TTG TCA GTA CCT ATA GTT CTG ACT GCG
 C   L   L   D   G   G   V   I   N   L   S   V   P   I   V   L   T   A 981             990             999             1008        1017            1026
ACT CAT GAA GAT AAA GAG AGG CTG GAC GGC TGT ACA GCA TTT GCT CTG ATG TAT
 T   H   E   D   K   E   R   L   D   G   C   T   A   F   A   L   M   Y 1035            1044            1053            1062        1071            1080
GAG GGC CGC CGT GTG GCC ATT CTT CGC AAT CCA GAG TTT TTT GAG CAC AGG AAA
 E   G   R   R   V   A   I   L   R   N   P   E   F   F   E   H   R   K 1089            1098            1107            1116        1125            1134
GAG GAG CGC TGT GCC AGA CAG TGG GGA ACG ACA TGC AAG AAC CAC CCC TAT ATT
 E   E   R   C   A   R   Q   W   G   T   T   C   K   N   H   P   Y   I
```

FIGURE 2C

```
              1143            1152            1161            1170            1179            1188
AAG ATG GTG ATG GAA CAA GGA GAT TGG CTG ATT GGA GGA GAT CTT CAA GTC TTG
 K   M   V   M   E   Q   G   D   W   L   I   G   G   D   L   Q   V   L 1197            1206            1215            1224            1233            1242
GAT CGA GTT TAT TGG AAT GAT GGT CTT GAT CAG TAT CGT CTT ACT CCT ACT GAG
 D   R   V   Y   W   N   D   G   L   D   Q   Y   R   L   T   P   T   E 1251            1260            1269            1278            1287            1296
CTA AAG CAG AAA TTT AAA GAT ATG AAT GCT GAT GCT GTC TTT GCA TTT CAA CTA
 L   K   Q   K   F   K   D   M   N   A   D   A   V   F   A   F   Q   L 1305            1314            1323            1332            1341            1350
CGC AAC CCA GTG CAC AAT GGA CAT GCC CTG TTA ATG CAG GAT ACC CAT AAG CAA
 R   N   P   V   H   N   G   H   A   L   L   M   Q   D   T   H   K   Q 1359            1368            1377            1386            1395            1404
CTT CTA GAG AGG GGC TAC CGG CGC CCT GTC CTC CTC CAC CCT CTG GGT GGC
 L   L   E   R   G   Y   R   R   P   V   L   L   H   P   L   G   G 1413            1422            1431            1440            1449            1458
TGG ACA AAG GAT GAC GAT GTT CCT TTG ATG TGG CGT ATG AAG CAG CAT GCT GCA
 W   T   K   D   D   D   V   P   L   M   W   R   M   K   Q   H   A   A 1467            1476            1485            1494            1503            1512
GTG TTG GAG GAA GGA GTT CTG AAT CCT GAG ACG ACA GTG GTG GCC ATC TTC CCA
 V   L   E   E   G   V   L   N   P   E   T   T   V   V   A   I   F   P
```

FIGURE 2D

```
      1521            1530            1539            1548            1557            1566
TCT CCC ATG ATG TAT GCT GGA CCA ACT GAG GTC CAG TGG CAT TGC AGA GCA CGG
 S   P   M   M   Y   A   G   P   T   E   V   Q   W   H   C   R   A   R 1575            1584            1593            1602            1611            1620
ATG GTT GCA GGA GCC AAC TTT TAC ATT GTT GGA CGA GAC CCT GCT GGC ATG CCT
 M   V   A   G   A   N   F   Y   I   V   G   R   D   P   A   G   M   P 1629            1638            1647            1656            1665            1674
CAT CCA GAA ACA GGG AAG GAT CTT TAT GAG CCA AGT CAT GGT GCC AAA GTG CTG
 H   P   E   T   G   K   D   L   Y   E   P   S   H   G   A   K   V   L 1683            1692            1701            1710            1719            1728
ACG ATG GCC CCT GGT TTA ATC ACT TTG GAA ATA GTT CCC TTT CGA GTT GCA GCT
 T   M   A   P   G   L   I   T   L   E   I   V   P   F   R   V   A   A 1737            1746            1755            1764            1773            1782
TAC AAC AAG AAA AAG CGT ATG GAC TAC TAT GAC TCT GAA CAC CAT GAA GAC
 Y   N   K   K   K   R   M   D   Y   Y   D   S   E   H   H   E   D 1791            1800            1809            1818            1827            1836
TTT GAA TTT ATT TCA GGA ACA CGA ATG CGC AAA CTT GCT CGA GAA GGC CAG AAA
 F   E   F   I   S   G   T   R   M   R   K   L   A   R   E   G   Q   K 1845            1854            1863            1872            1881            1890
CCA CCT GAA GGT TTC ATG GCT CCC AAG GCT TGG ACC GTG CTG ACA GAA TAC TAC
 P   P   E   G   F   M   A   P   K   A   W   T   V   L   T   E   Y   Y
```

FIGURE 2E

```
        1899           1908           1917      1926           1935      1944
AAA TCC TTG GAG AAA GCT TAG GCT GTT AAC CCA GTC ACT CCA CCT TTG ACA CAT
 K   S   L   E   K   A 1953           1962           1971      1980           1989      1998
TAC TAG TAA CAA GAG GGG ACC ACA TAG TCT CTG TTG GCA TTT CTT TGT GGT GTC 2007           2016           2025      2034           2043      2052
TGT CTG GAC ATG CTT CCT AAA AAC AGA CCA TTT TCC TTA ACT TGC ATC AGT TTT 2061           2070           2079      2088           2097      2106
GGT CTG CCT TAT GAG TTC TGT TTT GAA CAA GTG TAA CAC ACT GAT GGT TTT AAT 2115           2124           2133      2142           2151      2160
GTA TCT TTT CCA CTT ATT ATA GTT ATA TTC CTA CAA TAC AAT TTT AAA ATT GTC 2169           2178           2187      2196           2205      2214
TTT TTA TAT TAT ATT TAT GCT TCT GTG TCA TGA TTT TTT CAA GCT GTT ATA TTA 2223           2232           2241      2250           2259      2268
GTT GTA ACC AGT AGT ATT CAC ATT AAA TCT TGC TTT TTT TCC CCT TAA AAA AAG
```

FIGURE 2F

```
       2277           2286           2295           2304           2313           2322
AAA AAA ATT ACC AAA CAA TAA ACT TGG CTA GAC CTT GTT TTG AGG ATT TTA CAA 2331           2340           2349           2358           2367           2376
GAC CTT TGT AGC GAT TAG ATT TTT CTA CAT TGA AAA TAG AAA CTG CTT CCT 2385           2394           2403           2412           2421           2430
TTC TTC TTT CCA GTC AGC TAT TGG TCT TTC CAG CTG TTA TAA TCT AAA GTA TTC 2439           2448           2457           2466           2475           2484
TTA TGA TCT GTG TAA GCT CTG AAT GAA CTT CTT TAC TCA ATA AAA TTA ATT TTT 2493           2502
TGG CTT CTT AAA AAA AAA AAA AA 3'
```

FIGURE 2G

```
                                                        9          18          27          36          45          54
5' NNT GGT CTG GTC CCA TAT CAG AAG ACG TGA TTG GGT GAT GAC CAG TTA AAT GTA 63          72          81          90          99         108
   TTT GGA GAG GAC ACT ATG GGA GGT CCT GGC ATG GAA GAT TTG AGA AAG TGT AAA ATT
                            M   G   G   P   G   M   E   D   L   R   K   C   K   I 117         126         135         144         153         162
   ATT TTC ATA ATT GGT GGT CCT GGC TCT GGC AAA GGC ACA CAG TGT GAA AAG CTG
    I   F   I   I   G   G   P   G   S   G   K   G   T   Q   C   E   K   L 171         180         189         198         207         216
   GTG GAA AAA TAT GGA TTT ACA CAT CTC TCA ACT GGC GAG CTC CTG CGT GAG GAA
    V   E   K   Y   G   F   T   H   L   S   T   G   E   L   L   R   E   E 225         234         243         252         261         270
   CTG GCA TCA GAA TCT GAA AGA AGC AAA AAA TTG ATC AGA GAC ATT ATG GAA CGT GGA
    L   A   S   E   S   E   R   S   K   K   L   I   R   D   I   M   E   R   G 279         288         297         306         315         324
   GAC CTG GTG CCC TCA GGC ATC GTT TTG GAG CTC CTG AAG GAG GCC ATG GTG GCC
    D   L   V   P   S   G   I   V   L   E   L   L   K   E   A   M   V   A
```

FIGURE 3A

```
     333         342         351         360         369         378
AGC CTC GGG GAC ACC AGG GGC TTC CTG ATT GAC GGC TAT CCT CGG GAG GTG AAG
 S   L   G   D   T   R   G   F   L   I   D   G   Y   P   R   E   V   K 387         396         405         414         423         432
CAA GGG GAA GAG TTC GGA CGC AGG ATT GGA GAC CCA CAG TTG GTG ATC TGT ATG
 Q   G   E   E   F   G   R   R   I   G   D   P   Q   L   V   I   C   M 441         450         459         468         477         486
GAC TGC TCG GCA GAC ACC ATG ACC AAC CGC CTT CTC CAA AGG AGC CGG AGC AGC
 D   C   S   A   D   T   M   T   N   R   L   L   Q   R   S   R   S   S 495         504         513         522         531         540
CTG CCT GTG GAC GAC ACC ACC AAG ATC GCC ATC AAG CGC CTA GAA GCC TAC TAC
 L   P   V   D   D   T   T   K   I   A   I   K   R   L   E   A   Y   Y 549         558         567         576         585         594
CGA GCG TCC ATC CCC GTG ATC GCC TAC TAC GAG ACA AAA ACA CAG CTA CAC AAG
 R   A   S   I   P   V   I   A   Y   Y   E   T   K   T   Q   L   H   K 603         612         621         630         639         648
ATA AAT GCA GAG GGA ACA CCA GAG GAC GTT TTT CTT CAA CTC TGC ACA GCT ATT
 I   N   A   E   G   T   P   E   D   V   F   L   Q   L   C   T   A   I
```

FIGURE 3B

```
       657         666         675         684         693         702
GAC TCT ATT TTC TGA AGG CAA AAA TGC ATG TTT GTT AGA ATG GAA ACA GAA AAA
 D   S   I   F 711         720         729         738         747         756
CAT TAA AAA GTT CAT TCC TTA ACA CAA TGT TTC AAG TTA AAC CTT TTG TGT CAC 765         774         783         792         801         810
CGA CCC CAC CAA CCA CCT GCT AAA TCC TGA CAG CAC TGT CTT TTG CTT CCC AGC 819         828         837         846
TAG ACC TGT GTG AGA GGT GTC TGG AAA TCA TGC ATG GTG TAT TG 3'
```

FIGURE 3C

```
  1  MAKSPLEGVSSSRGLHAGRGPRRLSIEGNIAVGKSTFVKL  DRNK-1
  1  MAKSPLEGVSSSRGLHAGRGPRRLSIEGNIAVGKSTFVKL  g1480198
  1  MATPPKRSCPSFSASSEGTRIKKISIEGNIAAGKSTFVNI  g181510

41  LTKTYPEWHVATEPVATWQNIQAAGTQ---KACTAQSLGN  DRNK-1
 41  LTKTYPEWHVATEPVATWQNIQAAGTQ---KACTAQSLGN  g1480198
 41  LKQLCEDWEVVPEPVARWCNVQSTQDEFEELTMSQKNGGN  g181510

78  LLDMMYREPARWSYTFQTFSFLSRLKVQLEPFPEKLLQAR  DRNK-1
 78  LLDMMYREPARWSYTFQTFSFLSRLKVQLEPFPEKLLQAR  g1480198
 81  VLQMMYEKPERWSFTFQTYACLSRIRAQLASLNGKLKDAE  g181510

118  KPVQIFERSVYSDRYIFAKNLFENGSLSDISSGI-SIRTG  DRNK-1
118  KPVQIFERSVYSDRYIFAKNLFENDSLSDIEWHIYQDWHS  g1480198
121  KPVLFFERSVYSDRYIFASNLYESECMNETEWTIYQDWHD  g181510
```

FIGURE 4A

```
157 I L - - F S C G S L P A G S H Y M A S S T S R L L P R F V L K K L Y Q R A R E   DRNK-1
158 F L L W E F A S R I T L H G F I Y L Q A S - - - - P Q V C L K R L Y Q R A R E   g1480198
161 W M N N Q F G Q S L E L D G I I Y L Q A T - - - - P E T C L H R I Y L R G R N   g181510

194 E E K G I E L A Y L E Q L H G Q H E A W L I H K T T K L H F E A L M N I P V L V   DRNK-1
193 E E G I E L A Y L E Q L H G Q H E A W L I H K T T K L H F E A L M N I P V L V   g1480198
196 E E Q G I P L E Y L E K L H Y K H E S W L L H R T L K T N F D Y L Q E V P I L T   g181510

234 L D V N D D F S E E V T K Q E D L M R E V N T F V K N L                           DRNK-1
233 L D V N D D F S E E V T K Q E D L M R E V N T F V K N L                           g1480198
236 L D V N E D F K D - - - K Y E S L V E K V K E F L S T L                           g181510
```

FIGURE 4B

```
  1  M E I P G S L C K K V K L S N N A Q N W G M Q R A T N V T Y Q A H H V S R N K R   DRNK-2
  1  M E I P G S L C K K V K L S N N A Q N W G M Q R A T N V T Y Q A H H V S R N K R   g1109676
  1  M A F - - - - - - - - - - - L P N G - - - - Q L A T N V T F Q T Q H V S R A K R   g705385

41  G Q V V G T R G G F R G C T V W L T G L S G A G K T T V S M A L E E Y L V C H G   DRNK-2
 41  G Q V V G T R G G F R G C T V W L T G L S G A G K T T V S M A L E E Y L V C H G   g1109676
 26  G Q V L G Q R G G F R G C T V W F T G L S G A G K T T I S F A L E E Y L V S Q G   g705385

81  I P C Y T L D G D N I R Q G L N K N L G F S P E D R E E N V R R I A E V A K L F   DRNK-2
 81  I P C Y T L D G D N I R Q G L N K N L G F S P E D R E E N V R R I A E V A K L F   g1109676
 66  I P T Y S L D G D N V R H G L N K N L G F T Q E D R E E N I R R I S E V A K L F   g705385

121  A D A G L V C I T S F I S P Y T Q D R N N A R Q I H E G A S L P F F E V F V D A   DRNK-2
121  A D A G L V C I T S F I S P Y T Q D R N N A R Q I H E G A S L P F F E V F V D A   g1109676
106  A D G G I V C L T S F I S P F K R D L A R S L H E Q A G L P F F E C F V D T   g705385

161  P L H V C E Q R D V K G L Y K K A R A G E I K G F T G I D S E Y E K P E A P E L   DRNK-2
161  P L H V C E Q R D V K G L Y K K A R A G E I K G F T G I D S E Y E K P E A P E L   g1109676
146  P L D V C E Q R D V K G L Y K K A R A G Q I K G F T G I D Q Q Y E S P D A P E I   g705385
```

FIGURE 5A

```
201  V L K T D S C D V N D C V Q Q V V E L L Q E R D I V P V D A S Y E V K E L Y V V P   DRNK-2
201  V L K T D S C D V N D C V Q Q V V E L L Q E R D I V P V D A S Y E V K E L Y V V P   g1109676
186  Q L Y A G N K S I D E C V Q E V V S L L Q K N G V V P E S A V N I V K E L F V P     g705385

241  E N K L H L A K T D A E T L P A L K I N K V D M Q W V Q V L A E G W A T P L N G     DRNK-2
241  E N K L H L A K T D A E A L P A L K I N K V D M Q W V Q V L A E G W A T P L N G     g1109676
226  E S G L E H A K A E I V D L P T M E I T K L D T Q W V S E G W A T P L T G           g705385

281  F M R E R E Y L Q C L H F D C L L D G G V I N L S V P I V L T A T H E D K E R L     DRNK-2
281  F M R E R E Y L Q C L H F D C L L D G G V I N L S V P I V L T A T H E D K E R L     g1109676
266  F M R E R E Y L Q S Q H F G C L L D G G V T N Q S I P I V L P V H T A D K D R L     g705385

321  D G C T A F A L M Y E G R R V A I L R N P E F F E H R K E E R C A R Q W G T T C     DRNK-2
321  D G C T A F A L V Y E G R R V A I L R N P E F F E H R K E E R C A R Q W G T T C     g1109676
306  E G S S A F A L S Y E G K R I A I L R T P E F Y E H R K E E R C S R Q F G T S N     g705385

361  K N H P Y I K M V M E Q G D W L I G G D L Q V L D R V Y W N D G L D Q Y R L T P     DRNK-2
361  K N H P Y I K M V L E Q G D W L I G G D L Q V L D R I Y W N D G L D Q Y R L T P     g1109676
346  A G Q P Y V K M I M E S G D W L V G G D L E V L E R I T W N D G L D E Y R L T P     g705385
```

FIGURE 5B

```
401  T E L K Q K F K D M N A D A V F A F Q L R N P V H N G H A L L M Q D T H K Q L L    DRNK-2
401  T E L K Q K F K D M N A D A V F A F Q L R N P V H N G H A L L M Q D T H K Q L L    g1109676
386  N E L R A K F R A L N A D A V F A F Q L R N P V H N G H A L L M T D T R R R L T    g705385

441  E R G Y R R P V L L L H P L G G W T K D D D V P L M W R M K Q H A A V L E E G V    DRNK-2
441  E R G Y R R P V L L L H P L G G W T K D D D V P L M W R M K Q H A A V L E E G I    g1109676
426  E R G Y K K P V L L L H P L G G W T K D D D V P L A W R M K Q H Q A I L D E K V    g705385

481  L N P E T T V V A I F P S P M M Y A G P T E V Q W H C R A R M V A G A N F Y I V    DRNK-2
481  L D P E T T V V A I F P S P M M Y A G P T E V Q W H C R A R M V A G A N F Y I V    g1109676
466  L D P D Y T V M A I F P S P M M Y A G P T E V Q W H A K A R M S T G A N F Y I V    g705385

521  G R D P A G M P H P E T G K D L Y E P S H G A K V L T M A P G L I T L E I V P F    DRNK-2
521  G R D P A G M P H P E T G K D L Y E P T H G A K V L T M A P G L I T L E I V P F    g1109676
506  G R D P A G M P H P E T K Q D L Y N A T H G A K V L T M A P G L T Q L E I V P F    g705385

561  R V A A Y N K K K K R M D Y Y D S E H H E D F E F I S G T R M R K L A R E G Q K    DRNK-2
561  R V A A Y N K K K K R M D Y Y D S E H H E D F E F I S G T R M R K L A R E G Q K    g1109676
546  R V A A Y N K T K S A M D F Y D P E R H D E F M F I S G T K M R G M A R A G E T    g705385

601  P P E G F M A P K A W T V L T E Y Y K S - L E K A                                  DRNK-2
601  P P E G F M A P K A W T V L V E Y Y K S - L E K A                                  g1109676
586  P P N G F M A P S A W K I M V E Y Y K T K A Q Q S                                  g705385
```

FIGURE 5C

```
                                                                          DRNK-3
  1  M G G F M E D L R K C K I I F I I G G P G S G K G T Q C E K L V E K Y G F T H L  DRNK-3
  1  M E - - E K L K K T K I I F V V G G P G S G K G T Q C E K I V Q K Y G Y T H L  g178322
  1  M S T - - E K L K H H K I I F V V G G P G S G K G T Q C E K I V H K Y G Y T H L  g222786

41  S T G E L L R E E L A S E S E R S K L I R D I M E R G D L V P S G I V L E L L K  DRNK-3
 38  S T G D L L R S E V S S G S A R G K K L S E I M E K G Q L V P L E T V L D M L R  g178322
 39  S T G D L L R A E V S S G S E R G K K L Q A I M E K G E L V P L D T V L D M L R  g222786

81  E A M V A S L G D T R G F L I D G Y P R E V K Q G E E F G R R I G D P Q L V I C  DRNK-3
 78  D A M V A K V N T S K G F L I D G Y P R E V Q Q G E E F E R R I G Q P T L L L Y  g178322
 79  D A M L A K A D T S K G F L I D G Y P R E V K Q G E E F K K I A P P T L L L Y  g222786

121  M D C S A D T M T N R L L Q R S R S S L P V D D T T K T I A K R L E A Y Y R A S  DRNK-3
118  V D A G P E T M T Q R L L K R G E T S G R V D D N E E T I K K R L E T Y Y K A T  g178322
119  V D A G K E T M V K R L L K R G E T S G R V D D N E E T I K K R L E T Y Y K A T  g222786

161  I P V I A Y Y E T K T Q L H K I N A E G T P E D V F L Q L C T A I D S I F  DRNK-3
158  E P V I A F Y E K R G I V R K V N A E G S V D S V F S Q V C T H L D A L K  g178322
159  E P V I A F Y K G R G I V R Q L N A E G T V D E V F Q Q V C S Y L D K L  g222786
```

FIGURE 6

DISEASE RELATED NUCLEOTIDE KINASES

FIELD OF THE INVENTION

This invention relates to nucleic acid and amino acid sequences of disease related nucleotide kinases and to the use of these sequences in the diagnosis, prevention, and treatment of cancer, immune disorders, and neurological disorders.

BACKGROUND OF THE INVENTION

The nucleotide kinases play a key role in nucleotide metabolism and are crucial to the synthesis and regulation of cellular levels of the nucleoside triphosphates (ATP, GTP, CTP, and UTP) and their corresponding deoxynucleoside triphosphates. These molecules are all precursors in DNA and RNA synthesis in growing cells. In addition, ATP provides the primary source of biochemical energy in cells, and GTP is important in signal transduction pathways. Inhibition of various steps in the synthesis of nucleoside triphosphates has been the basis of many antiproliferative drugs for cancer and antiviral therapy.

All nucleotide kinases catalyze the transfer of a terminal phosphate residue from ATP or GTP to a nucleoside or nucleotide substrate. The individual enzymes are categorized primarily on the basis of their primary substrates.

Nucleoside kinases perform the first step in the nucleotide kinase "cascade" by phosphorylating various nucleosides. These nucleoside monophosphates become substrates for further phosphorylation to di- and triphosphates. Some nucleoside kinases have a rather broad substrate specificity. Human deoxycytidine kinase (dCK), for example, phosphorylates not only dC, but also dA, dG and various analogs of these natural nucleosides (Chottiner, E. G. et al. (1991) Proc. Natl. Acad. Sci. 88:1531–35). Similarly, deoxyguanosine kinase (dGK) has an overlapping substrate specificity with dCK and its activity is often indistinguishable from that of the latter enzyme. However, dCK is found at much higher levels in proliferating cells and lymphoid tissues, while dGK is the only deoxynucleoside kinase found in non-dividing nerve cells and muscle cells (Wang, L. et al. (1996) FEBS 390:39–43).

Adenylate kinase (AK) is found in almost all cell types and is especially abundant in cells having high rates of ATP synthesis and utilization such as skeletal muscle. In these cells, AK is physically associated with mitochondria and myofibrils, the subcellular structures that are involved in energy production and utilization, respectively. AK catalyzes the reversible transfer of a phosphate moiety between three adenine nucleotides; AMP, ADP, and ATP. Recent studies have demonstrated a major function for AK in transferring high energy phosphoryls from metabolic processes generating ATP to cellular components consuming ATP (Zeleznikar, R. J. et al (1995) J Biol Chem 270(13): 7311–7319). Thus AK may have a pivitol role in maintaining energy production in cells, particularly those having a high rate of growth or metabolism such as cancer cells, and may provide a target for suppression of its activity to treat certain cancers. Alternatively, reduced AK activity may be a source of various metabolic, muscle-energy disorders that can result in cardiac or respiratory failure. A rare form of hereditary hemolytic anemia is associated with AK deficiency in erythrocytes and is caused by a single amino acid substitution of $R_{128}$ to W (Matsuura, S. et al. (1989) J. Biol. Chem. 264:10148–55). Three isozymes of AK have been identified in vertebrates; AK1, AK2, and AK3. AK1 is present in the cytosol of skeletal muscle, brain, and erythrocytes. AK2 is found in the intermembrane space of mitochondria of liver, kidney, and heart. AK3 is found in the mitochondrial matrix of liver and heart and uses GTP as the phosphate donor.

In addition to providing a key step in the synthesis of GTP for RNA and DNA synthesis, guanylate kinase (GuK) also fulfills an essential function in signal transduction pathways of cells through the regulation of GDP and GTP. Specifically, GTP binding to a G protein mediates the activation of cell receptors, subsequent intracellular activation of adenyl cyclase, and production of the second messenger, cyclic AMP. GDP binding to G protein inhibits the process. GDP and GTP levels also control the activity of certain oncogenic proteins such as $p21^{ras}$ known to be involved in control of cell proliferation and oncogenesis (Bos, J. L. (1989) Cancer Res 49: 4682–9). High ratios of GTP:GDP caused by suppression of GuK causes activation of $p21^{ras}$ and promotes oncogenesis. Increasing GuK activity to increase levels of GDP and reduce the GTP:GDP ratio may provide a therapeutic strategy to reverse oncogenesis.

A specialized type of nucleotide kinase is adenosine 5'-phosphosulfate (APS) kinase that provides activated sulfate for various physiological reactions, such as synthesis of the amino acid cysteine. APS kinase transfers phosphate from ATP to the 3' position of APS forming the activated sulfate donor, adenosine 3'-phosphate 5'-phosphosulfate (PAPS). PAPS synthesis involves the sequential action of two enzyme activities; ATP sulfurylase, which catalyzes the formation of APS from ATP and free sulfate, and APS kinase which phosphorylates APS to PAPS (Li, H. et al. (1995) J. Biol. Chem. 270:29453–59). In mouse, ATP sulfurylase and APS kinase exist as a single bifunctional enzyme (PAPS synthetase) with the N-terminal portion of the molecule providing the APS kinase activity, and the C-terminal portion the ATP sulfurylase. A short segment of some 37 amino acids separates the two functional regions.

In addition to their natural substrates, the various kinases described above phosphorylate and activate a number of nucleotide homologs useful in antiviral and anticancer therapy. GuK phosphorylates and activates certain drugs useful in the treatment of viral infections, including anti-HSV drugs, acyclovir and buciclovir, and the anti-HIV drug, carbovir (Miller, W. H. and Miller R. L. (1980) J Biol Chem 255:7204–7; Stenberg, K. et al (1986) J Biol Chem 261: 2134–9). dCK phosphorylates a variety of antiviral and anticancer drugs including cytosine arabinoside and dideoxycytidine (Chottiner, et al. supra).

The discovery of new disease related nucleotide kinases and the polynucleotides encoding them satisfies a need in the art by providing new compositions which are useful in the diagnosis, prevention and treatment of cancer, immune disorders, and neurological disorders.

SUMMARY OF THE INVENTION

The invention features substantially purified polypeptides, disease related nucleotide kinases, collectively referred to as DRNK and individually as DRNK-1, DRNK-2 and DRNK-3, having the amino acid sequence shown in SEQ ID NO:1, SEQ ID NO:3, or SEQ ID NO:5, respectively, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding DRNK-1 under conditions suitable for the expression of the polypeptide; and b) recovering the polypeptide from the host cell culture.

The invention also provides a pharmaceutical composition comprising a substantially purified DRNK-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising at least a fragment of the amino acid sequence of SEQ ID NO:1.

Still further, the invention provides a purified agonist the polypeptide of SEQ ID NO:1.

The invention also provides a method for treating or preventing cancer comprising administering to a subject in need of such treatment an effective amount of a purified antagonist of DRNK-1.

The invention also provides a method for treating or preventing an immune disorder comprising administering to a subject in need of such treatment an effective amount of a purified antagonist of DRNK-1.

The invention also provides a method for detecting a polynucleotide which encodes DRNK-1 in a biological sample comprising the steps of: a) hybridizing a polynucleotide sequence complementary to the polynucleotide encoding DRNK-1 (SEQ ID NO:1) to nucleic acid material of a biological sample, thereby forming a hybridization complex; and b) detecting the hybridization complex, wherein the presence of the complex correlates with the presence of a polynucleotide encoding DRNK-1 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4 or variants thereof. In addition, the invention provides a polynucleotide sequence which hybridizes under stringent conditions to the polynucleotide sequence of SEQ ID NO:4.

In another aspect the invention provides a composition comprising an isolated and purified polynucleotide sequence comprising the complement of SEQ ID NO:4, or fragments or variants thereof. The invention also provides a polynucleotide sequence comprising the complement of SEQ ID NO:4.

The invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding DRNK-2 under conditions suitable for the expression of the polypeptide; and b) recovering the polypeptide from the host cell culture.

The invention also provides a pharmaceutical composition comprising a substantially purified DRNK-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising at least a fragment of the amino acid sequence of SEQ ID NO:3.

Still further, the invention provides a purified agonist of the polypeptide of SEQ ID NO:3.

The invention also provides a method for treating or preventing cancer comprising administering to a subject in need of such treatment an effective amount of a purified antagonist of DRNK-2.

The invention also provides a method for treating or preventing an immune disorder comprising administering to a subject in need of such treatment an effective amount of the purified antagonist of DRNK-2.

The invention also provides a method for detecting a polynucleotide which encodes DRNK-2 in a biological sample comprising the steps of: a) hybridizing a polynucleotide sequence complementary to the polynucleotide encoding DRNK-2 (SEQ ID NO:3) to nucleic acid material of a biological sample, thereby forming a hybridization complex; and b) detecting the hybridization complex, wherein the presence of the complex correlates with the presence of a polynucleotide encoding DRNK-2 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:5 or fragments thereof and a composition comprising said polynucleotide sequence. The invention also provides a polynucleotide sequence which hybridizes under stringent conditions to the polynucleotide sequence encoding the amino acid sequence SEQ ID NO:5, or fragments of said polynucleotide sequence. The invention further provides a polynucleotide sequence comprising the complement of the polynucleotide sequence encoding the amino acid sequence of SEQ ID NO: 5, or fragments or variants of said polynucleotide sequence.

The invention also provides an isolated and purified sequence comprising SEQ ID NO:6 or variants thereof. In addition, the invention provides a polynucleotide sequence which hybridizes under stringent conditions to the polynucleotide sequence of SEQ ID NO:6.

In another aspect the invention provides a composition comprising an isolated and purified polynucleotide sequence comprising the complement of SEQ ID NO:6, or fragments or variants thereof. The invention also provides a polynucleotide sequence comprising the complement of SEQ ID NO:6.

The invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:5 or a fragment thereof, the method comprising the steps of: a) culturing the host cell containing an expression vector containing at least a fragment of the polynucleotide sequence encoding DRNK-3 under conditions suitable for the expression of the polypeptide; and b) recovering the polypeptide from the host cell culture.

The invention also provides a pharmaceutical composition comprising a substantially purified DRNK-3 having the amino acid sequence of SEQ ID NO:5 in conjunction with a suitable pharmaceutical carrier.

The invention also provides a purified antagonist the polypeptide of SEQ ID NO:5. In one aspect the invention provides a purified antibody which binds to a polypeptide comprising at least a fragment of the amino acid sequence of SEQ ID NO:5.

Still further, the invention provides a purified agonist of the polypeptide of SEQ ID NO:5.

The invention also provides a method for treating or preventing a neurological disorder comprising administering to a subject in need of such treatment an effective amount of a pharmaceutical composition comprising purified DRNK-3.

The invention also provides a method for treating or preventing an immune disorder comprising administering to a subject in need of such treatment an effective amount of a purified antagonist of DRNK-3.

The invention also provides a method for detecting a polynucleotide which encodes DRNK-3 in a biological sample comprising the steps of: a) hybridizing a polynucleotide sequence complementary to the polynucleotide sequence encoding DRNK-3 (SEQ ID NO:5) to nucleic acid material of a biological sample, thereby forming a hybridization complex; and b) detecting the hybridization complex, wherein the presence of the complex correlates with the presence of a polynucleotide encoding DRNK-3 in the biological sample. In one aspect the nucleic acid material of the biological sample is amplified by the polymerase chain reaction prior to hybridization.

BRIEF DESCRIPTION OF THE FIGURES

FIGS. 1A, 1B, and 1C show the amino acid sequence (SEQ ID NO:1) and nucleic acid sequence (SEQ ID NO:2) of DRNK-1. The alignment was produced using MacDNASIS PRO™ software (Hitachi Software Engineering Co. Ltd. San Bruno, Calif.).

FIGS. 2A, 2B, 2C, 2D, 2E, 2F and 2G show the amino acid sequence (SEQ ID NO:3) and nucleic acid sequence (SEQ ID NO:4) of DRNK-2. The alignment was produced using MacDNASIS PRO™ software.

FIGS. 3A, 3B, and 3C show the amino acid sequence (SEQ ID NO:5) and nucleic acid sequence (SEQ ID NO:6) of DRNK-3. The alignment was produced using MacDNASIS PRO™ software.

FIGS. 4A and 4B show the amino acid sequence alignments among DRNK-1 (SEQ ID NO: 1), human deoxyguanosine kinase, dGK (GI 1480198; SEQ ID NO:7) and human deoxycytidine kinase, dCK(GI 181510; SEQ ID NO:8), produced using the multisequence alignment program of DNASTAR™ software (DNASTAR Inc, Madison Wis.).

FIGS. 5A, 5B, and 5C show the amino acid sequence alignments among DRNK-2 (SEQ ID NO:3), and PAPS synthetase from mouse (GI 1109676; SEQ ID NO:9) and marine worm (GI 705385; SEQ ID NO:10), produced using the multisequence alignment program of DNASTAR™ software.

FIG. 6 shows the amino acid sequence alignments among DRNK-3 (SEQ ID NO:5), and adenylate kinase from human (GI 178322; SEQ ID NO:11) and chicken (GI 222786; SEQ ID NO:12), produced using the multisequence alignment program of DNASTAR™ software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

DRNK, as used herein, refers to the amino acid sequences of substantially purified DRNK obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to DRNK, increases or prolongs the duration of the effect of DRNK. Agonists may include proteins, nucleic acids, carbohydrates, or any other molecules which bind to and modulate the effect of DRNK.

An "allele" or "allelic sequence", as used herein, is an alternative form of the gene encoding DRNK. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding DRNK as used herein include those with deletions, insertions, or substitutions of different nucleotides resulting in a polynucleotide that encodes the same or a functionally equivalent DRNK. Included within this definition are polymorphisms which may or may not be readily detectable using a particular oligonucleotide probe of the polynucleotide encoding DRNK, and improper or unexpected hybridization to alleles, with a locus other than the normal chromosomal locus for the polynucleotide sequence encoding DRNK. The encoded protein may also be "altered" and contain deletions, insertions, or substitutions of amino acid residues which produce a silent change and result in a functionally equivalent DRNK. Deliberate amino acid substitutions may be made on the basis of similarity in polarity, charge, solubility, hydrophobicity, hydrophilicity, and/or the amphipathic nature of the residues as long as the biological or immunological activity of DRNK is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of DRNK are preferably about 5 to about 15 amino acids in length and retain the biological activity or the immunological activity of DRNK. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to DRNK, decreases the amount or the duration of the effect of the biological or immunological activity of DRNK. Antagonists may include proteins, nucleic acids, carbohydrates, or any other molecules which decrease the effect of DRNK.

As used herein, the term "antibody" refers to intact molecules as well as fragments thereof, such as Fa, F(ab')$_2$, and Fv, which are capable of binding the epitopic determinant. Antibodies that bind DRNK polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic DRNK, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding DRNK (SEQ ID NO:1, SEQ ID NO:3, or SEQ ID NO:5) or fragments thereof (e.g., SEQ ID NO:2, SEQ ID NO:4, or SEQ ID NO:6 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn. in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding DRNK in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to DRNK or the encoded DRNK. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to a high-density array of distinct polynucleotides or oligonucleotides synthesized on a substrate, such as paper, nylon or other type of membrane, filter, chip, glass slide, or any other suitable solid support.

The term "modulate", as used herein, refers to a change in the activity of DRNK. For example, modulation may cause an increase or a decrease in protein activity, binding characteristics, or any other biological, functional or immunological properties of DRNK.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1, SEQ ID NO:3, or SEQ ID NO:5" encompasses the full-length DRNK and fragments thereof.

The term "sample", as used herein, is used in its broadest sense. A biological sample suspected of containing nucleic acid encoding DRNK, or fragments thereof, or DRNK itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of DRNK, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human disease related nucleotide kinases (hereinafter referred to as "DRNK"), the polynucleotides encoding DRNK, and the use of these compositions for the diagnosis, prevention, or treatment of cancer, immune disorders, and neurological disorders.

Nucleic acids encoding the DRNK-1 of the present invention were first identified in Incyte Clone 56821 from the fibroblast cDNA library (FIBRNOT 01) using a computer search for amino acid sequence alignments. A consensus sequence, SEQ ID NO:2, was derived from the following overlapping and/or extended nucleic acid sequences: Incyte Clones 56821/FIBRNOT01, 122980/LUNGNOT01, 363392/PROSNOT01, 365693/SYNORAT01, 389627/THYMNOT02, 815619/OVARTUT01, 1356718/LUNGNOT09, and 1373746/BSTMNON02.

In one embodiment, the invention encompasses a polypeptide comprising the amino acid sequence of SEQ ID NO:1, as shown in FIG. 1. DRNK-1 is 261 amino acids in length and has a potential ATP/GTP binding site (p-loop) at $G_{28}$NIAVGK. A potential N-myristoylation site is found at $G_8$, and a potential N-glycosylation site is located at $N_{141}$. The N-terminal 25 amino acids constitute a mitochondrial localization signal with important basic residues located within it at $K_3$, $R_{13}$, $R_{19}$, $R_{22}$, and $R_{23}$. As shown in FIG. 4, DRNK-1 has chemical and structural homology with human dGK (GI 1480198; SEQ ID NO:7) and dCK (GI 181510; SEQ ID NO:8). In particular, DRNK-1 shares 88% and 43% identity with dGK and dCK, respectively. dGk and dCK both share the ATP/GTP-binding motif (p-loop) found in DRNK-1, and dGK shares the mitochondrial localization signal and the potential N-myristoylation and N-glycosylation sites found in DRNK-1. Northern analysis shows the expression of this sequence in various libraries, at least 28% of which are immortalized or cancerous and at least 19% of which involve inflammation or the immune response.

Nucleic acids encoding the DRNK-2 of the present invention were first identified in Incyte Clone 373887 from the lung tissue cDNA library (LUNGNOT02) using a computer search for amino acid sequence alignments. A consensus sequence, SEQ ID NO:4, was derived from the following overlapping and/or extended nucleic acid sequences: Incyte Clones 373887/LUNGNOT02, 413040/BRSTNOT01, 491900/HNT2NOT01, 830200/PROSTUT04, 1405393/LATRTUT02, and 1728108/PROSNOT14.

In another embodiment, the invention encompasses a polypeptide comprising the amino acid sequence of SEQ ID NO:3, as shown in FIG. 2. DRNK-2 is 624 amino acids in length and has a potential ATP/GTP binding site (p-loop) at $G_{59}$LSGAGKT, and potential N-glycosylation sites at $N_{27}$ and $N_{303}$. A PAPS-dependent enzyme motif is found at $K_{176}$ARAGEIKGFTG. An ATP pyrophosphatase PP-motif, common to many ATP sulfurylases, extends between $N_{411}$ and $M_{433}$. As shown in FIG. 5, DRNK-2 has chemical and structural homology with PAPS synthetase from mouse (GI 1109676; SEQ ID NO:9) and marine worm (GI 705385; SEQ ID NO:10). In particular, DRNK-2 shares 99% and 72% identity with mouse and marine worm PAPS synthetase, respectively. Both PAPS synthetases share the ATP/GTP-binding motif (p-loop), the PAPS-dependent enzyme motif, the PP-motif, and the two N-glycosylation sites found in DRNK-2. Northern analysis shows the expression of this sequence in various libraries, at least 33% of which are immortalized or cancerous and at least 27% of which involve inflammation or the immune response.

Nucleic acids encoding the DRNK-3 of the present invention were first identified in Incyte Clone 1484821 from the brain, corpus callosum cDNA library (CORPNOT02) using a computer search for amino acid sequence alignments. A consensus sequence, SEQ ID NO:6, was derived from the following overlapping and/or extended nucleic acid sequences: Incyte Clones 447668/TLYMNOT02, 661593/BRAINOT03, and 1484821/CORPNOT02.

In another embodiment, the invention encompasses a polypeptide comprising the amino acid sequence of SEQ ID NO:5, as shown in FIG. 3. DRNK-3 is 197 amino acids in length and has a potential adenylate kinase signature sequence at $F_{93}$LIDGYPREVKQ, a potential internal myristoylation site at $G_{18}$, and a potential tyrosine kinase phosphorylation site at $K_{151}$. As shown in FIG. 6, DRNK-3 has chemical and structural homology with adenylate kinase from human (GI 178322; SEQ ID NO:11) and chicken (GI 222786; SEQ ID NO:12). In particular, DRNK-3 shares 58% and 55% identity with human and chicken AK, respectively. Both the human and chicken AK share the three structural motifs identified above in DRNK-3. In addition, DRNK-3 and the human and chicken AK share the essential arginine residue, $R_{131}$, necessary for an active AK. Northern analysis shows the expression of this sequence in brain tissue (Alzheimer's disease) and lymphocytes.

The invention also encompasses DRNK variants. A preferred DRNK variant is one having at least 80%, and more preferably 90%, amino acid sequence identity to the DRNK amino acid sequence (SEQ ID NO:1, SEQ ID NO:3, or SEQ ID NO:5). A most preferred DRNK variant is one having at least 95% amino acid sequence identity to SEQ ID NO:1, SEQ ID NO:3, or SEQ ID NO:5.

The invention also encompasses polynucleotides which encode DRNK. Accordingly, any nucleic acid sequence which encodes the amino acid sequence of DRNK can be used to produce recombinant molecules which express DRNK. In a particular embodiment, the invention encompasses the polynucleotide comprising the nucleic acid sequence of SEQ ID NO:2, SEQ ID NO:4, or SEQ ID NO:6 as shown in FIG. 1, FIG. 2, and FIG. 3, respectively.

It will be appreciated by those skilled in the art that as a result of the degeneracy of the genetic code, a multitude of nucleotide sequences encoding DRNK, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring DRNK, and all such variations are to be considered as being specifically disclosed.

Although nucleotide sequences which encode DRNK and its variants are preferably capable of hybridizing to the nucleotide sequence of the naturally occurring DRNK under appropriately selected conditions of stringency, it may be advantageous to produce nucleotide sequences encoding DRNK or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding DRNK and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode DRNK and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding DRNK or any fragment thereof.

Also encompassed by the invention are polynucleotide sequences that are capable of hybridizing to the claimed nucleotide sequences, and in particular, those shown in SEQ ID NO:2, SEQ ID NO:4, or SEQ ID NO:6, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (U.S. Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding DRNK may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length CDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode DRNK may be used in recombinant DNA molecules to direct expression of DRNK, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express DRNK.

As will be understood by those of skill in the art, it may be advantageous to produce DRNK-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter DRNK encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding DRNK may be ligated to a heterologous sequence to encode a fusion protein. For example, to screen peptide libraries for inhibitors of DRNK activity, it may be useful to encode a chimeric DRNK protein that can be recognized by a commercially available antibody. A fusion protein may also be engineered to contain a cleavage site located between the DRNK encoding sequence and the heterologous protein sequence, so that DRNK may be cleaved and purified away from the heterologous moiety.

In another embodiment, sequences encoding DRNK may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of DRNK, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of DRNK, or any part thereof, may be altered during direct synthesis and/or combined using chemical methods with sequences from other proteins, or any part thereof, to produce a variant polypeptide.

In order to express a biologically active DRNK, the nucleotide sequences encoding DRNK or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding DRNK and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding DRNK. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding DRNK, vectors based on SV40 or EBV may be used with an appropriate selectable marker.

In bacterial systems, a number of expression vectors may be selected depending upon the use intended for DRNK. For example, when large quantities of DRNK are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding DRNK may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding DRNK may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express DRNK. For example, in one such system, *Autographa californica* nuclear polyhedrosis virus (AcNPV) is used as a vector to express foreign genes in *Spodoptera frugiperda* cells or in Trichoplusia larvae. The sequences encoding DRNK may be cloned into a non-essential region of the virus, such as the polyhedrin gene, and placed under control of the polyhedrin promoter. Successful insertion of DRNK will render the polyhedrin gene inactive and produce recombinant virus lacking coat protein. The recombinant viruses may then be used to infect, for example, *S. frugiperda* cells or Trichoplusia larvae in which DRNK may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding DRNK may be ligated into an adenovirus transcription/translation complex consisting of the late promoter and tripartite leader sequence. Insertion in a non-essential E1 or E3 region of the viral genome may be used to obtain a viable virus which is capable of expressing DRNK in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding DRNK. Such signals include the ATG initiation codon and adjacent sequences. In cases where sequences encoding DRNK, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express DRNK may be transformed using expression vectors which may contain viral origins of replication and/or endogenous expression elements and a selectable marker gene on the same or on a separate vector.

Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding DRNK is inserted within a marker gene sequence, transformed cells containing sequences encoding DRNK can be identified by the absence of marker gene function. Alternatively, a marker gene can be placed in tandem with a sequence encoding DRNK under the control of a single promoter. Expression of the marker gene in response to induction or selection usually indicates expression of the tandem gene as well.

Alternatively, host cells which contain the nucleic acid sequence encoding DRNK and express DRNK may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding DRNK can be detected by DNA-DNA or DNA-RNA hybridization or amplification using probes or fragments or fragments of polynucleotides encoding DRNK. Nucleic acid amplification based assays involve the use of oligonucleotides or oligomers based on the sequences encoding DRNK to detect transformants containing DNA or RNA encoding DRNK.

A variety of protocols for detecting and measuring the expression of DRNK, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on DRNK is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding DRNK include oligolabeling, nick translation, end-labeling or PCR amplification using a labeled nucleotide. Alternatively, the sequences encoding DRNK, or any fragments thereof may be cloned into a vector for the production of an MRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Miss.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding DRNK may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode DRNK may be designed to contain signal sequences which direct secretion of DRNK through a prokaryotic or eukaryotic cell membrane. Other constructions may be used to join sequences encoding DRNK to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and DRNK may be used to facilitate purification. One such expression vector provides for expression of a fusion protein containing DRNK and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying DRNK from the fusion protein. A discussion of vectors which contain fusion proteins is provided in Kroll, D. J. et al. (1993; DNA Cell Biol. 12:441–453).

In addition to recombinant production, fragments of DRNK may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of DRNK may be chemically synthesized separately and combined using chemical methods to produce the full length molecule.

Therapeutics

Chemical and structural homology exits among DRNK-1 and dGK from human (GI 1480198) and dCK from human (GI 181510). In addition, DRNK-1 is expressed in tissues associated with cancer and the immune response. Therefore, DRNK-1 appears to play a role in cancer and immune disorders, particularly disorders in which DRNK-1 is overexpressed.

Therefore, in one embodiment, an antagonist of DRNK-1 may be administered to a subject to prevent or treat cancer. Cancers may include, but are not limited to adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector expressing the complement of the polynucleotide encoding DRNK-1 may be administered to a subject to treat or prevent any cancer including, but not limited to, the types of cancer described above.

In another embodiment, an antagonist of DRNK-1 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding DRNK-1 may be administered to a subject to treat or prevent an immune disorder including, but not limited to, any of the immune disorders described above.

In one aspect, antibodies which specifically bind DRNK-1 may be used directly as an antagonist or indirectly as a targeting or delivery mechanism for bringing a pharmaceutical agent to cells or tissue which express DRNK-1.

Chemical and structural homology exits among DRNK-2 and PAPS synthetase from mouse (GI 1109676) and marine worm (GI 705385). In addition, DRNK-2 is expressed in tissues associated with cancer and the immune response. Therefore, DRNK-2 appears to play a role in cancer and immune disorders, particularly disorders in which DRNK-2 is overexpressed.

Therefore, in another embodiment, an antagonist of DRNK-2 may be administered to a subject to prevent or treat cancer. Cancers may include, but are not limited to adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector expressing the complement of the polynucleotide encoding DRNK-2 may be administered to a subject to treat or prevent cancer including, but not limited to, the types of cancer described above.

In another embodiment, an antagonist of DRNK-2 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding DRNK-2 may be administered to a subject to treat or prevent an immune disorder including, but not limited to, any of the immune disorders described above.

In one aspect, antibodies which specifically bind DRNK-2 may be used directly as an antagonist or indirectly as a targeting or delivery mechanism for bringing a pharmaceutical agent to cells or tissue which express DRNK-2.

Chemical and structural homology exits among DRNK-3 and adenylate kinase from human (GI 178322) and chicken (GI 222786). In addition, DRNK-3 is expressed in tissues associated with the brain and the immune response. Therefore, DRNK-3 appears to play a role in neurological and immune disorders. In particular, a decrease in the level or activity of DRNK-3 appears to be associated with neurological disorders, while an increase in the level or activity of DRNK-3 appears to be associated with immune disorders.

Therefore, in another embodiment, DRNK-3 or a fragment or derivative thereof may be administered to a subject to prevent or treat a neurological disorder. Such disorders may include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder.

In another embodiment, a vector capable of expressing DRNK-3, or a fragment or a derivative thereof, may also be administered to a subject to prevent or treat a neurological disorder including, but not limited to, those described above.

In still another embodiment, an agonist which modulates the activity of DRNK-3 may also be administered to a subject to prevent or treat a neurological disorder including, but not limited to, those described above.

In another embodiment, an antagonist of DRNK-3 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding DRNK-3 may be administered to a subject to treat or prevent an immune disorder including, but not limited to, any of the immune disorders described above.

In one aspect, antibodies which specifically bind DRNK-3 may be used directly as an antagonist or indirectly as a targeting or delivery mechanism for bringing a pharmaceutical agent to cells or tissue which express DRNK-3.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of DRNK may be produced using methods which are generally known in the art. In particular, purified DRNK may be used to produce antibodies or to screen libraries of pharmaceutical agents to identify those which specifically bind DRNK.

Antibodies to DRNK may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with DRNK or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to DRNK have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of DRNK amino acids may be fused with those of another protein such as keyhole limpet hemocyanin and antibody produced against the chimeric molecule.

Monoclonal antibodies to DRNK may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce DRNK-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for DRNK may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between DRNK and its specific antibody. A two-site, monoclonal-based immunoassay utilizing monoclonal antibodies reactive to two non-interfering DRNK epitopes is preferred, but a competitive binding assay may also be employed (Maddox, supra).

In another embodiment of the invention, the polynucleotides encoding DRNK, or any fragment or complement thereof, may be used for therapeutic purposes. In one aspect, the complement of the polynucleotide encoding DRNK may be used in situations in which it would be desirable to block the transcription of the mRNA. In particular, cells may be transformed with sequences complementary to polynucleotides encoding DRNK. Thus, complementary molecules or fragments may be used to modulate DRNK activity, or to achieve regulation of gene function. Such technology is now well known in the art, and sense or antisense oligonucleotides or larger fragments, can be designed from various locations along the coding or control regions of sequences encoding DRNK.

Expression vectors derived from retro viruses, adenovirus, herpes or vaccinia viruses, or from various bacterial plasmids may be used for delivery of nucleotide sequences to the targeted organ, tissue or cell population.

Methods which are well known to those skilled in the art can be used to construct vectors which will express nucleic acid sequence which is complementary to the polynucleotides of the gene encoding DRNK. These techniques are described both in Sambrook et al. (supra) and in Ausubel et al. (supra).

Genes encoding DRNK can be turned off by transforming a cell or tissue with expression vectors which express high levels of a polynucleotide or fragment thereof which encodes DRNK. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding DRNK (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding DRNK.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding DRNK. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of DRNK, antibodies to DRNK, mimetics, agonists, antagonists, or inhibitors of DRNK. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol;

starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of DRNK, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example DRNK or fragments thereof, antibodies of DRNK, agonists, antagonists or inhibitors of DRNK, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind DRNK may be used for the diagnosis of conditions or diseases characterized by expression of DRNK, or in assays to monitor patients being treated with DRNK, agonists, antagonists or inhibitors. The antibodies useful for diagnostic purposes may be prepared in the same manner as those described above for therapeutics. Diagnostic assays for DRNK include methods which utilize the antibody and a label to detect DRNK in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring DRNK are known in the art and provide a basis for diagnosing altered or abnormal levels of DRNK expression. Normal or standard values for DRNK expression are established by combining body fluids or cell extracts taken from normal mammalian subjects, preferably human, with antibody to DRNK under conditions suitable for complex formation The amount of standard complex formation may be quantified by various methods, but preferably by photometric, means. Quantities of DRNK expressed in subject, control and disease, samples from biopsied tissues are compared with the standard values. Deviation between standard and subject values establishes the parameters for diagnosing disease.

In another embodiment of the invention, the polynucleotides encoding DRNK may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of DRNK may be correlated with disease. The diagnostic assay may be used to distinguish between absence, presence, and excess expression of DRNK, and to monitor regulation of DRNK levels during therapeutic intervention.

In one aspect, hybridization with PCR probes which are capable of detecting polynucleotide sequences, including genomic sequences, encoding DRNK or closely related molecules, may be used to identify nucleic acid sequences which encode DRNK. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding DRNK, alleles, or related sequences.

Probes may also be used for the detection of related sequences, and should preferably contain at least 50% of the nucleotides from any of the DRNK encoding sequences. The hybridization probes of the subject invention may be DNA or RNA and derived from the nucleotide sequence of SEQ ID NO:2, SEQ ID NO:4, or SEQ ID NO:6 or from genomic sequence including promoter, enhancer elements, and introns of the naturally occurring DRNK.

Means for producing specific hybridization probes for DNAs encoding DRNK include the cloning of nucleic acid sequences encoding DRNK or DRNK derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding DRNK may be used for the diagnosis of conditions, disorders, or diseases which are associated with expression of DRNK. Examples of such conditions or diseases include cancer such as cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; and neurological disorders such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder. The polynucleotide sequences encoding DRNK may be used in Southern or northern analysis, dot blot, or other membrane-based technologies; in PCR technologies; or in dipstick, pin, ELISA assays or microarrays utilizing fluids or tissues from patient biopsies to detect altered DRNK expression. Such qualitative or quantitative methods are well known in the art.

In a particular aspect, the nucleotide sequences encoding DRNK may be useful in assays that detect activation or induction of various cancers, particularly those mentioned above. The nucleotide sequences encoding DRNK may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding DRNK in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of DRNK, a normal or standard profile for expression is established. This may be accomplished by combining body fluids or cell extracts taken from normal subjects, either animal or human, with a sequence, or a fragment thereof, which encodes DRNK, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding DRNK may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of DRNK include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides derived from any of the polynucleotide sequences described herein may be used as probes in microarrays. The microarrays can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20 nucleotides in length. For a certain type of microarray, it may be preferable to use oligonucleotides which are only 7–10 nucleotides in length. The microarray may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from 2 to one million.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support.

In another aspect, the oligomers may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devises (slot blot or dot blot apparatus) materials and machines (including robotic instruments) and contain grids of 8 dots, 24 dots, 96 dots, 384 dots, 1536 dots or 6144 dots, or any other multiple which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode DRNK may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding DRNK on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, DRNK, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between DRNK and the agent being tested, may be measured.

Another technique for drug screening which may be used provides for high throughput screening of compounds having suitable binding affinity to the protein of interest as described in published PCT application WO84/03564. In this method, as applied to DRNK large numbers of different small test compounds are synthesized on a solid substrate, such as plastic pins or some other surface. The test compounds are reacted with DRNK, or fragments thereof, and washed. Bound DRNK is then detected by methods well known in the art. Purified DRNK can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding DRNK specifically compete with a test compound for binding DRNK. In this manner, the antibodies can be used to detect the presence of any peptide which shares one or more antigenic determinants with DRNK.

In additional embodiments, the nucleotide sequences which encode DRNK may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction
FIBRNOT01

The normal fibroblast cell FIBRNOT01 cDNA library was custom constructed by Stratagene (Stratagene, La Jolla, Calif. 92037) using mRNA purified from cultured WI-38 cells. The library was prepared by Stratagene essentially as described. The cDNA library was prepared by purifying poly(A+)RNA from human fibroblast cells and then enzymatically synthesizing double stranded complementary DNA (cDNA). Synthetic adaptor oligonucleotides were ligated onto the ends of the cDNA enabling its insertion into the lambda vector. The FIBRNOT01 library was constructed using the Uni-ZAP™ vector system (Stratagene).

The FIBRNOT01 cDNA library can be screened with either DNA probes or antibody probes and the pBluescript® phagemid (Stratagene) can be rapidly excised in vivo. The custom-constructed library phage particles were infected into E. coli host strain XL1-Blue® (Stratagene). Alternative unidirectional vectors might include, but are not limited to, pcDNAI (Invitrogen, San Diego, Calif.) and pSHlox-1 (Novagen, Madison Wis.).

LUNGNOT02

The LUNGNOT02 cDNA library was constructed from the normal lung tissue of a 47 year old male Caucasian (HEV082). The tissue was obtained from Keystone Skin Bank, International Institute for the Advancement of Medicine (Exton, Pa.). The frozen tissue was ground in a mortar and pestle and lysed immediately in a buffer containing guanidinium isothiocyanate. The lysate was extracted twice with phenol chloroform at pH 8.0 and centrifuged over a CsCl cushion using an Beckman SW28 rotor in a Beckman L8-70M Ultracentrifuge (Beckman Instruments). The RNA was precipitated using 0.3M sodium acetate and 2.5 volumes of ethanol, resuspended in water and DNase treated for 15 min at 37° C. The poly A+RNA was isolated using the Qiagen Oligotex kit (QIAGEN Inc, Chatsworth Calif.).

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated on Sephacryl S400 to obtain sequences which exceeded 1000 bp in size. The size selected cDNAs were inserted into the UniZap® vector system (Stratagene, La Jolla Calif.); and the vector, which contains the pBluescript™ phagemid (Stratagene), was transformed into cells of E. coli, strain XL1-BlueMRF™ (Stratagene).

CORPNOT02

The CORPNOT02 cDNA library was constructed from microscopically normal corpus callosum tissue removed from a 74-year-old Caucasian male (specimen #RA95-09-0670; International Institute for the Advancement of Medicine, Exton, Pa.) who died from Alzheimer's disease. Patient history included decubitus ulcers (bedsores) on the left hip and coccyx. Previous surgeries included prostate and urethral surgery.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. Extraction and precipitatation were repeated as before. The mRNA was then isolated using the Qiagen Oligotex kit (QIAGEN, Inc.; Chatsworth, Calif.) and used to construct the cDNA library.

The mRNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105-01; Pharmacia), and those cDNAs exceeding 400 bp were ligated into pSport I. The plasmid pSport I was subsequently transformed into DH5a™ competent cells (Cat. #18258-012; Gibco/BRL).

II Isolation and Sequencing of cDNA Clones

The phagemid forms of individual cDNA clones were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the pBluescript™ plasmid and the cDNA insert. The phagemid DNA was secreted from the cells and purified, then used to re-infect fresh host cells, where the double stranded phagemid DNA was produced. Because the phagemid carries the gene for β-lactamase, the newly-transformed bacteria are selected on medium containing ampicillin.

Phagemid DNA was purified using the Magic Minipreps™ DNA Purification System (catalogue #A7100. Promega Corp., Madison, Wis. 53711). The DNA was eluted from the purification resin already prepared for DNA sequencing and other analytical manipulations.

Phagemid DNA may also be purified using the QIAWELL-8 Plasmid or QIAGEN® DNA Purification System (QIAGEN Inc, Chatsworth, Calif.). The DNA was eluted from the purification resin and prepared for DNA sequencing and other analytical manipulations.

An alternative method for purifying phagemid DNA utilizes the Miniprep Kit available from Advanced Genetic Technologies Corp. (Gaithersburg, Md., Catalog No. 77468). This kit is in the 96-well format and provides enough reagents for 960 purifications. Each kit contains a recommended protocol, which is employed except for the following changes. First, the 96 wells are each filled with only 1 ml of sterile Terrific Broth (catalog #22711) with carbenicillin at 25 mg/L and glycerol at 0.4%. After the wells are inoculated, the bacteria are cultured for 24 hours and lysed with 60 μl of lysis buffer. A centrifugation step (2900 rpm for 5 minutes) is performed before the contents of the block is added to the primary filter plate. The optional step of adding isopropanol to TRIS buffer is not performed. After the last step in the protocol, samples are transferred to a Beckman 96-well block for storage.

Another alternative method for purifying phagemid DNA uses the REAL Prep 96 Plasmid Kit (Catalog #26173, QIAGEN, Inc.). This kit enables the simultaneous purification of 96 samples in a 96-well block using multi-channel reagent dispensers. The recommended protocol is employed except for the following changes: 1) the bacteria are cultured in 1 ml of sterile Terrific Broth (Catalog #22711, Gibco/BRL) with carbenicillin at 25 mg/L and glycerol at 0.4%; 2) after inoculation, the cultures are incubated for 19 hours and at the end of incubation, the cells are lysed with 0.3 ml of lysis buffer; and 3) following isopropanol precipitation, the plasmid DNA pellet is resuspended in 0.1 ml of distilled water. After the last step in the protocol, samples are transferred to a 96-well block for storage at 4° C.

III Homology Searching of cDNA Clones and Their Deduced Proteins

FIBRNOT01

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

LUNGNOT02 AND CORPNOT02

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Atschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding DRNK occurs. Abundance and percent abundance are also reported. Abundance directly reflects the number of times a particular transcript is represented in a cDNA library, and percent abundance is abundance divided by the total number of sequences examined in the cDNA library.

V Extension of DRNK Encoding Polynucleotides

The nucleic acid sequence of the Incyte Clone 56821, 373887, or 1484821 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C. the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well.

Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, SEQ ID NO:4, or SEQ ID NO:6 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the DRNK-encoding sequence, or any part thereof, is used to decrease or inhibit expression of naturally occurring DRNK. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of DRNK, SEQ ID NO:1, SEQ ID NO:3, or SEQ ID NO:5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the DRNK-encoding transcript.

IX Expression of DRNK

Expression of DRNK is accomplished by subcloning the cDNAs into appropriate vectors and transforming the vectors into host cells. In this case, the cloning vector is also used to express DRNK in E. coli. Upstream of the cloning site, this vector contains a promoter for $\beta$-galactosidase, followed by sequence containing the amino-terminal Met, and the subsequent seven residues of $\beta$-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of $\beta$-galactosidase, about 5 to 15 residues of linker, and the full length protein. The signal residues direct the secretion of DRNK into the bacterial growth media which can be used directly in the following assay for activity.

X Demonstration of DRNK Activity

The activity of DRNK-1 and DRNK-3 may be measured using a standard nucleotide kinase assay by the incorporation of $^{32}$p from gamma-labeled $^{32}$p -ATP into dGMP or ADP, respectively, using a gamma radioisotope counter. The enzyme, in an kinase buffer, is incubated together with the appropriate substrate (dG or AMP) and $P^{32}$-labeled ATP as the phosphate donor. The reaction is incubated at 37° C. and terminated by addition of trichloroacetic acid. The acid extract is neutralized and subjected to gel electrophoresis to separate the mono-, di-, and triphosphonucleotide fractions. The appropriate fraction (dGMP or ADP, respectively) is cut out and counted. The radioactivity recovered is proportional to the enzyme activity.

DRNK-2 activity is measured in a coupled assay that measures both ATP sulfurylase and APS kinase activity by the incorporation of $^{35}$S from $H_2^{35}SO_4$ into PAPS. DRNK-2 is incubated together with $H_2^{35}SO_4$, ATP, 20 mM $MgCl_2$, and Tris-HCl buffer (pH 8.0) and the reaction products are treated as described above. The radioactivity recovered in PAPS is proportional to the enzyme activity.

XI Production of DRNK Specific Antibodies

DRNK that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring DRNK Using Specific Antibodies

Naturally occurring or recombinant DRNK is substantially purified by immunoaffinity chromatography using antibodies specific for DRNK. An immunoaffinity column is constructed by covalently coupling DRNK antibody to an activated chromatographic resin, such as CNBr-activated Sepharose (Pharmacia & Upjohn). After the coupling, the resin is blocked and washed according to the manufacturer's instructions.

Media containing DRNK is passed over the immunoaffinity column, and the column is washed under conditions that allow the preferential absorbance of DRNK (e.g., high ionic strength buffers in the presence of detergent). The column is eluted under conditions that disrupt antibody/DRNK binding (eg, a buffer of pH 2–3 or a high concentration of a chaotrope, such as urea or thiocyanate ion), and DRNK is collected.

XIII Identification of Molecules Which Interact with DRNK

DRNK or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled DRNK, washed and any wells with labeled DRNK complex are assayed. Data obtained using different concentrations of DRNK are used to calculate values for the number, affinity, and association of DRNK with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide sequence encoding the deoxyguanosine kinase of SEQ ID NO:1.

2. A composition comprising the polynucleotide sequence of claim 2.

3. A polynucleotide sequence which is fully complementary to the polynucleotide sequence of claim 1.

4. An isolated and purified polynucleotide sequence comprising SEQ ID NO:2.

5. A composition comprising the polynucleotide sequence of claim 4.

6. A polynucleotide sequence which is fully complementary to the polynucleotide sequence of claim 4.

7. An expression vector containing the polynucleotide sequence of claim 1.

8. A host cell containing the vector of claim 7.

9. A method for producing a polypeptide comprising the amino acid sequence of SEQ ID NO: 1, the method comprising the steps of:
   a) culturing the host cell of claim 8 under conditions suitable for the expression of the polypeptide; and
   b) recovering the polypeptide from the host cell culture.

10. A method for detecting a polynucleotide which encodes a deoxyguanosine kinase in a biological sample comprising the steps of:
   a) hybridizing the polynucleotide of claim 3 to nucleic acid material of a biological sample, thereby forming a hybridization complex;
   b) washing the hybridization complex under stringent wash conditions of at least 0.1× saline sodium citrate and 0.5% sodium dodecyl sulfate; and
   c) detecting said hybridization complex, wherein the presence of said complex correlates with the presence of a polynucleotide encoding deoxyguanosine kinase in said biological sample.

11. The method of claim 10 wherein the nucleic acid material is amplified by the polymerase chain reaction prior to hybridization.

* * * * *

UNITED STATES PATENT AND TRADEMARK OFFICE
CERTIFICATE OF CORRECTION

PATENT NO. : 5,817,482
DATED : Oct. 6, 1998
INVENTOR(S) : Olga Bandman, Jennifer L. Hillman, Phillip R. Hawkins, Karl J. Guegler, Neil C. Corley It is certified that error appears in the above-indentified patent and that said Letters Patent is hereby corrected as shown below:

Col 65, line 30, delete "claim 2" and insert --claim 1--.

Signed and Sealed this

Ninth Day of November, 1999

Attest:

Q. TODD DICKINSON

Attesting Officer    Acting Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 261 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: FIBRNOT01
        ( B ) CLONE: 56821

( x i ) SEQUENCE DESCRIPTION: SEQ ID NO:1:

```
Met  Ala  Lys  Ser  Pro  Leu  Glu  Gly  Val  Ser  Ser  Ser  Arg  Gly  Leu  His
 1              5                        10                       15
Ala  Gly  Arg  Gly  Pro  Arg  Arg  Leu  Ser  Ile  Glu  Gly  Asn  Ile  Ala  Val
               20                       25                       30
Gly  Lys  Ser  Thr  Phe  Val  Lys  Leu  Leu  Thr  Lys  Thr  Tyr  Pro  Glu  Trp
              35                   40                        45
His  Val  Ala  Thr  Glu  Pro  Val  Ala  Thr  Trp  Gln  Asn  Ile  Gln  Ala  Ala
         50                   55                   60
Gly  Thr  Gln  Lys  Ala  Cys  Thr  Ala  Gln  Ser  Leu  Gly  Asn  Leu  Leu  Asp
 65                  70                       75                            80
```

| | | | | | | | | | | | | | | |
|---|---|---|---|---|---|---|---|---|---|---|---|---|---|---|
|Met|Met|Tyr|Arg|Glu<br>85|Pro|Ala|Arg|Trp|Ser<br>90|Tyr|Thr|Phe|Gln|Thr<br>95|Phe|

Met Met Tyr Arg Glu Pro Ala Arg Trp Ser Tyr Thr Phe Gln Thr Phe
            85                  90                  95
Ser Phe Leu Ser Arg Leu Lys Val Gln Leu Glu Pro Phe Pro Glu Lys
            100                 105                 110
Leu Leu Gln Ala Arg Lys Pro Val Gln Ile Phe Glu Arg Ser Val Tyr
            115                 120                 125
Ser Asp Arg Tyr Ile Phe Ala Lys Asn Leu Phe Glu Asn Gly Ser Leu
    130                 135                 140
Ser Asp Ile Ser Ser Gly Ile Ser Ile Arg Thr Gly Ile Leu Phe Ser
145                 150                 155                 160
Cys Gly Ser Leu Pro Ala Gly Ser His Tyr Met Ala Ser Ser Thr Ser
                165                 170                 175
Arg Leu Leu Pro Arg Phe Val Leu Lys Lys Leu Tyr Gln Arg Ala Arg
            180                 185                 190
Glu Glu Glu Lys Gly Ile Glu Leu Ala Tyr Leu Glu Gln Leu His Gly
            195                 200                 205
Gln His Glu Ala Trp Leu Ile His Lys Thr Thr Lys Leu His Phe Glu
    210                 215                 220
Ala Leu Met Asn Ile Pro Val Leu Val Leu Asp Val Asn Asp Asp Phe
225                 230                 235                 240
Ser Glu Glu Val Thr Lys Gln Glu Asp Leu Met Arg Glu Val Asn Thr
                245                 250                 255
Phe Val Lys Asn Leu
            260

(2) INFORMATION FOR SEQ ID NO:2:

(i) SEQUENCE CHARACTERISTICS:
       (A) LENGTH: 958 base pairs
       (B) TYPE: nucleic acid
       (C) STRANDEDNESS: single
       (D) TOPOLOGY: linear (vii) IMMEDIATE SOURCE:
       (A) LIBRARY: FIBRNOT01
       (B) CLONE: 56821

(xi) SEQUENCE DESCRIPTION: SEQ ID NO:2:

```
NTGCCCGTTA GGCCCCGTTA ACGCCTCTCC CTAAGTCGGC TTCGAGCACC CTTCAGTTCC      60
ATGGCCAAGA GCCCACTCGA GGGCGTTTCC TCCTCCAGAG GCCTGCACGC GGGGCGCGGG     120
CCCCGAAGGC TCTCCATCGA AGGCAACATT GCTGTGGGAA AGTCCACGTT TGTGAAGTTA     180
CTCACGAAAA CTTACCCAGA ATGGCACGTA GCTACAGAAC CTGTAGCAAC ATGGCAGAAT     240
ATCCAGGCTG CTGGCACCCA AAAGCCTGC ACTGCCCAAA GTCTTGGAAA CTTGCTGGAT      300
ATGATGTACC GGGAGCCAGC ACGATGGTCC TACACATTCC AGACATTTTC CTTTTTGAGC     360
CGCCTGAAAG TACAGCTGGA GCCCTTCCCT GAGAAACTCT TACAGGCCAG GAAGCCAGTA     420
CAGATCTTTG AGAGGTCTGT GTACAGTGAC AGGTATATCT TTGCAAAGAA TCTTTTTGAA     480
AATGGTTCCC TCAGTGACAT CTCGAGTGGC ATATCTATCA GGACTGGCAT TCTTTTCTCC     540
TGTGGGAGTT TGCCAGCCGG ATCACATTAC ATGGCTTCAT CTACCTCCAG GCTTCTCCCC     600
AGGTTTGTTT TGAAGAAACT GTACCAAAGG GCCAGGGAGG AGGAGAAAGG AATTGAGCTG     660
GCCTATCTAG AGCAGCTGCA TGGCCAACAC GAAGCCTGGC TTATTCACAA GACAACGAAG     720
CTCCACTTTG AGGCTCTGAT GAACATTCCA GTGCTGGTGT TGGATGTCAA TGATGATTTT     780
TCTGAGGAAG TAACCAAACA AGAAGACCTC ATGAGAGAGG TAAACACCTT TGTAAAGAAT     840
CTGTAACCAA TACCATGATG TTCAGGCTGT GATCTGGGCT CCCTGACTTT CTGAAGCTAG     900
```

```
AAAAATGTTG TGTCTCCCAA CCANCTTTCC ATCCCCAGCC CCTCTCATCC CTGGAGCA         958
```

( 2 ) INFORMATION FOR SEQ ID NO:3:

( i ) SEQUENCE CHARACTERISTICS:
        ( A ) LENGTH: 624 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: LUNGNOT02
        ( B ) CLONE: 373887

( x i ) SEQUENCE DESCRIPTION: SEQ ID NO:3:

```
Met Glu Ile Pro Gly Ser Leu Cys Lys Lys Val Lys Leu Ser Asn Asn
 1               5                  10                  15

Ala Gln Asn Trp Gly Met Gln Arg Ala Thr Asn Val Thr Tyr Gln Ala
             20                  25                  30

His His Val Ser Arg Asn Lys Arg Gly Gln Val Val Gly Thr Arg Gly
         35                  40                  45

Gly Phe Arg Gly Cys Thr Val Trp Leu Thr Gly Leu Ser Gly Ala Gly
     50                  55                  60

Lys Thr Thr Val Ser Met Ala Leu Glu Glu Tyr Leu Val Cys His Gly
 65                  70                  75                  80

Ile Pro Cys Tyr Thr Leu Asp Gly Asp Asn Ile Arg Gln Gly Leu Asn
                 85                  90                  95

Lys Asn Leu Gly Phe Ser Pro Glu Asp Arg Glu Glu Asn Val Arg Arg
            100                 105                 110

Ile Ala Glu Val Ala Lys Leu Phe Ala Asp Ala Gly Leu Val Cys Ile
        115                 120                 125

Thr Ser Phe Ile Ser Pro Tyr Thr Gln Asp Arg Asn Asn Ala Arg Gln
130                 135                 140

Ile His Glu Gly Ala Ser Leu Pro Phe Phe Glu Val Phe Val Asp Ala
145                 150                 155                 160

Pro Leu His Val Cys Glu Gln Arg Asp Val Lys Gly Leu Tyr Lys Lys
                165                 170                 175

Ala Arg Ala Gly Glu Ile Lys Gly Phe Thr Gly Ile Asp Ser Glu Tyr
            180                 185                 190

Glu Lys Pro Glu Ala Pro Glu Leu Val Leu Lys Thr Asp Ser Cys Asp
        195                 200                 205

Val Asn Asp Cys Val Gln Gln Val Val Glu Leu Leu Gln Glu Arg Asp
210                 215                 220

Ile Val Pro Val Asp Ala Ser Tyr Glu Val Lys Glu Leu Tyr Val Pro
225                 230                 235                 240

Glu Asn Lys Leu His Leu Ala Lys Thr Asp Ala Glu Thr Leu Pro Ala
                245                 250                 255

Leu Lys Ile Asn Lys Val Asp Met Gln Trp Val Gln Val Leu Ala Glu
            260                 265                 270

Gly Trp Ala Thr Pro Leu Asn Gly Phe Met Arg Glu Arg Glu Tyr Leu
        275                 280                 285

Gln Cys Leu His Phe Asp Cys Leu Leu Asp Gly Gly Val Ile Asn Leu
290                 295                 300

Ser Val Pro Ile Val Leu Thr Ala Thr His Glu Asp Lys Glu Arg Leu
305                 310                 315                 320

Asp Gly Cys Thr Ala Phe Ala Leu Met Tyr Glu Gly Arg Arg Val Ala
                325                 330                 335
```

```
Ile  Leu  Arg  Asn  Pro  Glu  Phe  Phe  Glu  His  Arg  Lys  Glu  Glu  Arg  Cys
               340                     345                     350

Ala  Arg  Gln  Trp  Gly  Thr  Thr  Cys  Lys  Asn  His  Pro  Tyr  Ile  Lys  Met
          355                     360                     365

Val  Met  Glu  Gln  Gly  Asp  Trp  Leu  Ile  Gly  Gly  Asp  Leu  Gln  Val  Leu
     370                     375                     380

Asp  Arg  Val  Tyr  Trp  Asn  Asp  Gly  Leu  Asp  Tyr  Arg  Leu  Thr  Pro
385                      390                     395                     400

Thr  Glu  Leu  Lys  Gln  Lys  Phe  Lys  Asp  Met  Asn  Ala  Asp  Ala  Val  Phe
               405                     410                     415

Ala  Phe  Gln  Leu  Arg  Asn  Pro  Val  His  Asn  Gly  His  Ala  Leu  Leu  Met
               420                     425                     430

Gln  Asp  Thr  His  Lys  Gln  Leu  Leu  Glu  Arg  Gly  Tyr  Arg  Arg  Pro  Val
          435                     440                     445

Leu  Leu  Leu  His  Pro  Leu  Gly  Gly  Trp  Thr  Lys  Asp  Asp  Val  Pro
450                      455                     460

Leu  Met  Trp  Arg  Met  Lys  Gln  His  Ala  Ala  Val  Leu  Glu  Glu  Gly  Val
465                      470                     475                     480

Leu  Asn  Pro  Glu  Thr  Thr  Val  Val  Ala  Ile  Phe  Pro  Ser  Pro  Met  Met
                    485                     490                     495

Tyr  Ala  Gly  Pro  Thr  Glu  Val  Gln  Trp  His  Cys  Arg  Ala  Arg  Met  Val
               500                     505                     510

Ala  Gly  Ala  Asn  Phe  Tyr  Ile  Val  Gly  Arg  Asp  Pro  Ala  Gly  Met  Pro
               515                     520                     525

His  Pro  Glu  Thr  Gly  Lys  Asp  Leu  Tyr  Glu  Pro  Ser  His  Gly  Ala  Lys
          530                     535                     540

Val  Leu  Thr  Met  Ala  Pro  Gly  Leu  Ile  Thr  Leu  Glu  Ile  Val  Pro  Phe
545                      550                     555                     560

Arg  Val  Ala  Ala  Tyr  Asn  Lys  Lys  Lys  Arg  Met  Asp  Tyr  Tyr  Asp
                    565                     570                     575

Ser  Glu  His  His  Glu  Asp  Phe  Glu  Phe  Ile  Ser  Gly  Thr  Arg  Met  Arg
               580                     585                     590

Lys  Leu  Ala  Arg  Glu  Gly  Gln  Lys  Pro  Pro  Glu  Gly  Phe  Met  Ala  Pro
          595                     600                     605

Lys  Ala  Trp  Thr  Val  Leu  Thr  Glu  Tyr  Tyr  Lys  Ser  Leu  Glu  Lys  Ala
610                      615                     620
```

( 2 ) INFORMATION FOR SEQ ID NO:4:

( i ) SEQUENCE CHARACTERISTICS:
    ( A ) LENGTH: 2506 base pairs
    ( B ) TYPE: nucleic acid
    ( C ) STRANDEDNESS: single
    ( D ) TOPOLOGY: linear ( v i i ) IMMEDIATE SOURCE:
    ( A ) LIBRARY: LUNGNOT02
    ( B ) CLONE: 373887

( x i ) SEQUENCE DESCRIPTION: SEQ ID NO:4:

```
CAGAGAACCC  CGGCTGCTCA  GCGCGCTCCG  CGGTCATGGA  GATCCCCGGG  AGCCTGTGCA      60

AGAAAGTCAA  GCTGAGCAAT  AACGCGCAGA  ACTGGGGAAT  GCAGAGAGCA  ACCAATGTCA     120

CCTACCAAGC  CCATCATGTC  AGCAGGAACA  AGAGAGGTCA  GGTGGTGGGG  ACCAGAGGTG     180

GCTTTCGTGG  TTGCACAGTT  TGGCTAACAG  GCTTGTCTGG  AGCGGGAAAG  ACTACTGTGA     240

GCATGGCCTT  GGAGGAGTAC  CTGGTTTGTC  ATGGTATTCC  ATGCTACACT  CTGGATGGTG     300
```

| | | | | | |
|---|---|---|---|---|---|
|ACAATATTCG|TCAAGGTCTC|AATAAAAATC|TTGGCTTTAG|TCCTGAAGAC|AGAGAAGAGA 360|
|ATGTTCGACG|CATCGCAGAA|GTTGCTAAAC|TGTTTGCAGA|TGCTGGCTTA|GTGTGCATCA 420|
|CAAGTTTCAT|ATCACCTTAC|ACTCAGGATC|GCAACAATGC|AAGGCAAATT|CATGAAGGTG 480|
|CAAGTTTACC|GTTTTTTGAA|GTATTTGTTG|ATGCTCCTCT|GCATGTTTGT|GAACAGAGGG 540|
|ATGTCAAAGG|ACTCTACAAA|AAAGCCCGGG|CAGGAGAAAT|TAAAGGTTTC|ACTGGGATCG 600|
|ATTCTGAATA|TGAAAAGCCA|GAGGCCCCTG|AGTTGGTGCT|GAAAACAGAC|TCCTGTGATG 660|
|TAAATGACTG|TGTCCAGCAA|GTTGTGGAAC|TTCTACAGGA|ACGGGATATT|GTACCTGTGG 720|
|ATGCATCTTA|TGAAGTAAAA|GAACTATATG|TGCCAGAAAA|TAAACTTCAT|TTGGCAAAAA 780|
|CAGATGCGGA|AACATTACCA|GCACTGAAAA|TTAATAAAGT|GGATATGCAG|TGGGTGCAGG 840|
|TTTTGGCAGA|AGGTTGGGCA|ACCCCATTGA|ATGGCTTTAT|GAGAGAGAGG|GAGTACTTGC 900|
|AGTGCCTTCA|TTTTGATTGT|CTTCTGGATG|GAGGTGTCAT|TAACTTGTCA|GTACCTATAG 960|
|TTCTGACTGC|GACTCATGAA|GATAAAGAGA|GGCTGGACGG|CTGTACAGCA|TTTGCTCTGA 1020|
|TGTATGAGGG|CCGCCGTGTG|GCCATTCTTC|GCAATCCAGA|GTTTTTGAG|CACAGGAAAG 1080|
|AGGAGCGCTG|TGCCAGACAG|TGGGGAACGA|CATGCAAGAA|CCACCCCTAT|ATTAAGATGG 1140|
|TGATGGAACA|AGGAGATTGG|CTGATTGGAG|GAGATCTTCA|AGTCTTGGAT|CGAGTTTATT 1200|
|GGAATGATGG|TCTTGATCAG|TATCGTCTTA|CTCCTACTGA|GCTAAAGCAG|AAATTTAAAG 1260|
|ATATGAATGC|TGATGCTGTC|TTTGCATTTC|AACTACGCAA|CCCAGTGCAC|AATGGACATG 1320|
|CCCTGTTAAT|GCAGGATACC|CATAAGCAAC|TTCTAGAGAG|GGGCTACCGG|CGCCCTGTCC 1380|
|TCCTCCTCCA|CCCTCTGGGT|GGCTGGACAA|AGGATGACGA|TGTTCCTTTG|ATGTGGCGTA 1440|
|TGAAGCAGCA|TGCTGCAGTG|TTGGAGGAAG|GAGTTCTGAA|TCCTGAGACG|ACAGTGGTGG 1500|
|CCATCTTCCC|ATCTCCCATG|ATGTATGCTG|GACCAACTGA|GGTCCAGTGG|CATTGCAGAG 1560|
|CACGGATGGT|TGCAGGAGCC|AACTTTTACA|TTGTTGGACG|AGACCCTGCT|GGCATGCCTC 1620|
|ATCCAGAAAC|AGGGAAGGAT|CTTTATGAGC|CAAGTCATGG|TGCCAAAGTG|CTGACGATGG 1680|
|CCCCTGGTTT|AATCACTTTG|GAAATAGTTC|CCTTTCGAGT|TGCAGCTTAC|AACAAGAAAA 1740|
|AGAAGCGTAT|GGACTACTAT|GACTCTGAAC|ACCATGAAGA|CTTTGAATTT|ATTTCAGGAA 1800|
|CACGAATGCG|CAAACTTGCT|CGAGAAGGCC|AGAAACCACC|TGAAGGTTTC|ATGGCTCCCA 1860|
|AGGCTTGGAC|CGTGCTGACA|GAATACTACA|AATCCTTGGA|GAAAGCTTAG|GCTGTTAACC 1920|
|CAGTCACTCC|ACCTTTGACA|CATTACTAGT|AACAAGAGGG|GACCACATAG|TCTCTGTTGG 1980|
|CATTTCTTTG|TGGTGTCTGT|CTGGACATGC|TTCCTAAAAA|CAGACCATTT|TCCTTAACTT 2040|
|GCATCAGTTT|TGGTCTGCCT|TATGAGTTCT|GTTTTGAACA|AGTGTAACAC|ACTGATGGTT 2100|
|TTAATGTATC|TTTTCCACTT|ATTATAGTTA|TATTCCTACA|ATACAATTTT|AAAATTGTCT 2160|
|TTTTATATTA|TATTTATGCT|TCTGTGTCAT|GATTTTTCA|AGCTGTTATA|TTAGTTGTAA 2220|
|CCAGTAGTAT|TCACATTAAA|TCTTGCTTTT|TTTCCCCTTA|AAAAAGAAA|AAAATTACCA 2280|
|AACAATAAAC|TTGGCTAGAC|CTTGTTTTGA|GGATTTTACA|AGACCTTTGT|AGCGATTAGA 2340|
|TTTTTTTTCT|ACATTGAAAA|TAGAAACTGC|TTCCTTTCTT|CTTTCCAGTC|AGCTATTGGT 2400|
|CTTTCCAGCT|GTTATAATCT|AAAGTATTCT|TATGATCTGT|GTAAGCTCTG|AATGAACTTC 2460|
|TTTACTCAAT|AAAATTAATT|TTTTGGCTTC|TTAAAAAAAA|AAAAAA| 2506|

( 2 ) INFORMATION FOR SEQ ID NO:5:

( i ) SEQUENCE CHARACTERISTICS:
        ( A ) LENGTH: 197 amino acids
        ( B ) TYPE: amino acid ( C ) STRANDEDNESS: single
( D ) TOPOLOGY: linear ( v i i ) IMMEDIATE SOURCE:
( A ) LIBRARY: CORPNOT02
( B ) CLONE: 1484821

( x i ) SEQUENCE DESCRIPTION: SEQ ID NO:5:

```
Met Gly Gly Phe Met Glu Asp Leu Arg Lys Cys Lys Ile Ile Phe Ile
 1               5                  10                  15
Ile Gly Gly Pro Gly Ser Gly Lys Gly Thr Gln Cys Glu Lys Leu Val
                20                  25                  30
Glu Lys Tyr Gly Phe Thr His Leu Ser Thr Gly Glu Leu Leu Arg Glu
            35                  40                  45
Glu Leu Ala Ser Glu Ser Glu Arg Ser Lys Leu Ile Arg Asp Ile Met
        50                  55                  60
Glu Arg Gly Asp Leu Val Pro Ser Gly Ile Val Leu Glu Leu Leu Lys
65                  70                  75                  80
Glu Ala Met Val Ala Ser Leu Gly Asp Thr Arg Gly Phe Leu Ile Asp
                85                  90                  95
Gly Tyr Pro Arg Glu Val Lys Gln Gly Glu Glu Phe Gly Arg Arg Ile
                100                 105                 110
Gly Asp Pro Gln Leu Val Ile Cys Met Asp Cys Ser Ala Asp Thr Met
                115                 120                 125
Thr Asn Arg Leu Leu Gln Arg Ser Arg Ser Ser Leu Pro Val Asp Asp
            130                 135                 140
Thr Thr Lys Thr Ile Ala Lys Arg Leu Glu Ala Tyr Tyr Arg Ala Ser
145                 150                 155                 160
Ile Pro Val Ile Ala Tyr Tyr Glu Thr Lys Thr Gln Leu His Lys Ile
                165                 170                 175
Asn Ala Glu Gly Thr Pro Glu Asp Val Phe Leu Gln Leu Cys Thr Ala
                180                 185                 190
Ile Asp Ser Ile Phe
            195
```

( 2 ) INFORMATION FOR SEQ ID NO:6:

( i ) SEQUENCE CHARACTERISTICS:
( A ) LENGTH: 852 base pairs
( B ) TYPE: nucleic acid
( C ) STRANDEDNESS: single
( D ) TOPOLOGY: linear ( v i i ) IMMEDIATE SOURCE:
( A ) LIBRARY: CORPNOT02
( B ) CLONE: 1484821

( x i ) SEQUENCE DESCRIPTION: SEQ ID NO:6:

```
TGGTCTGGTC CCATATCAGA AGACGTGATT GGGTGATGAC CAGTTAAATG TATTTGGAGA      60
GGACACTATG GGAGGTTTCA TGGAAGATTT GAGAAAGTGT AAAATTATTT TCATAATTGG     120
TGGTCCTGGC TCTGGCAAAG GCACACAGTG TGAAAAGCTG GTGGAAAAAT ATGGATTTAC     180
ACATCTCTCA ACTGGCGAGC TCCTGCGTGA GGAACTGGCA TCAGAATCTG AAAGAAGCAA     240
ATTGATCAGA GACATTATGG AACGTGGAGA CCTGGTGCCC TCAGGCATCG TTTTGGAGCT     300
CCTGAAGGAG GCCATGGTGG CCAGCCTCGG GGACACCAGG GGCTTCCTGA TTGACGGCTA     360
TCCTCGGGAG GTGAAGCAAG GGGAAGAGTT CGGACGCAGG ATTGGAGACC CACAGTTGGT     420
GATCTGTATG GACTGCTCGG CAGACACCAT GACCAACCGC CTTCTCCAAA GGAGCCGGAG     480
CAGCCTGCCT GTGGACGACA CCACCAAGAC CATCGCCAAG CGCCTAGAAG CCTACTACCG     540
```

```
AGCGTCCATC  CCCGTGATCG  CCTACTACGA  GACAAAAACA  CAGCTACACA  AGATAAATGC    600
AGAGGGAACA  CCAGAGGACG  TTTTTCTTCA  ACTCTGCACA  GCTATTGACT  CTATTTTCTG    660
AAGGCAAAAA  TGCATGTTTG  TTAGAATGGA  AACAGAAAAA  CATTAAAAAG  TTCATTCCTT    720
AACACAATGT  TTCAAGTTAA  ACCTTTTGTG  TCACCGACCC  CACCAACCAC  CACCTGCTAA    780
ATCCTGACAG  CACTGTTTGC  TTCCCAGCTA  GACCTGTGTG  AGAGGTGTCT  GGAAATCATG    840
CATGGTGTAT  TG                                                           852
```

( 2 ) INFORMATION FOR SEQ ID NO:7:

( i ) SEQUENCE CHARACTERISTICS:
        ( A ) LENGTH: 260 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1480198

( x i ) SEQUENCE DESCRIPTION: SEQ ID NO:7:

```
Met  Ala  Lys  Ser  Pro  Leu  Glu  Gly  Val  Ser  Ser  Arg  Gly  Leu  His
 1              5                   10                       15
Ala  Gly  Arg  Gly  Pro  Arg  Arg  Leu  Ser  Ile  Glu  Gly  Asn  Ile  Ala  Val
            20                   25                       30
Gly  Lys  Ser  Thr  Phe  Val  Lys  Leu  Leu  Thr  Lys  Thr  Tyr  Pro  Glu  Trp
           35                   40                       45
His  Val  Ala  Thr  Glu  Pro  Val  Ala  Thr  Trp  Gln  Asn  Ile  Gln  Ala  Ala
        50                   55                       60
Gly  Thr  Gln  Lys  Ala  Cys  Thr  Ala  Gln  Ser  Leu  Gly  Asn  Leu  Leu  Asp
65                        70                       75                       80
Met  Met  Tyr  Arg  Glu  Pro  Ala  Arg  Trp  Ser  Tyr  Thr  Phe  Gln  Thr  Phe
               85                       90                       95
Ser  Phe  Leu  Ser  Arg  Leu  Lys  Val  Gln  Leu  Glu  Pro  Phe  Pro  Glu  Lys
              100                      105                      110
Leu  Leu  Gln  Ala  Arg  Lys  Pro  Val  Gln  Ile  Phe  Glu  Arg  Ser  Val  Tyr
              115                      120                      125
Ser  Asp  Arg  Tyr  Ile  Phe  Ala  Lys  Asn  Leu  Phe  Glu  Asn  Asp  Ser  Leu
              130                      135                      140
Ser  Asp  Ile  Glu  Trp  His  Ile  Tyr  Gln  Asp  Trp  His  Ser  Phe  Leu  Leu
145                      150                      155                     160
Trp  Glu  Phe  Ala  Ser  Arg  Ile  Thr  Leu  His  Gly  Phe  Ile  Tyr  Leu  Gln
                        165                      170                     175
Ala  Ser  Pro  Gln  Val  Cys  Leu  Lys  Arg  Leu  Tyr  Gln  Arg  Ala  Arg  Glu
                        180                      185                      190
Glu  Glu  Glu  Gly  Ile  Glu  Leu  Ala  Tyr  Leu  Glu  Gln  Leu  His  Gly  Gln
              195                      200                      205
His  Glu  Ala  Trp  Leu  Ile  His  Lys  Thr  Thr  Lys  Leu  His  Phe  Glu  Ala
        210                      215                      220
Leu  Met  Asn  Ile  Pro  Val  Leu  Val  Leu  Asp  Val  Asn  Asp  Asp  Phe  Ser
225                      230                      235                     240
Glu  Glu  Val  Thr  Lys  Gln  Glu  Asp  Leu  Met  Arg  Glu  Val  Asn  Thr  Phe
                        245                      250                      255
Val  Lys  Asn  Leu
              260
```

-continued ( 2 ) INFORMATION FOR SEQ ID NO:8:

( i ) SEQUENCE CHARACTERISTICS:
        ( A ) LENGTH: 260 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 181510

( x i ) SEQUENCE DESCRIPTION: SEQ ID NO:8:

```
Met  Ala  Thr  Pro  Pro  Lys  Arg  Ser  Cys  Pro  Ser  Phe  Ser  Ala  Ser  Ser
 1              5                        10                       15
Glu  Gly  Thr  Arg  Ile  Lys  Lys  Ile  Ser  Ile  Glu  Gly  Asn  Ile  Ala  Ala
                 20                       25                   30
Gly  Lys  Ser  Thr  Phe  Val  Asn  Ile  Leu  Lys  Gln  Leu  Cys  Glu  Asp  Trp
             35                       40                   45
Glu  Val  Val  Pro  Glu  Pro  Val  Ala  Arg  Trp  Cys  Asn  Val  Gln  Ser  Thr
         50                       55                   60
Gln  Asp  Glu  Phe  Glu  Glu  Leu  Thr  Met  Ser  Gln  Lys  Asn  Gly  Gly  Asn
 65                       70                   75                           80
Val  Leu  Gln  Met  Met  Tyr  Glu  Lys  Pro  Glu  Arg  Trp  Ser  Phe  Thr  Phe
                 85                       90                   95
Gln  Thr  Tyr  Ala  Cys  Leu  Ser  Arg  Ile  Arg  Ala  Gln  Leu  Ala  Ser  Leu
             100                      105                  110
Asn  Gly  Lys  Leu  Lys  Asp  Ala  Glu  Lys  Pro  Val  Leu  Phe  Phe  Glu  Arg
             115                      120                  125
Ser  Val  Tyr  Ser  Asp  Arg  Tyr  Ile  Phe  Ala  Ser  Asn  Leu  Tyr  Glu  Ser
         130                      135                  140
Glu  Cys  Met  Asn  Glu  Thr  Glu  Trp  Thr  Ile  Tyr  Gln  Asp  Trp  His  Asp
145                       150                      155                      160
Trp  Met  Asn  Asn  Gln  Phe  Gly  Gln  Ser  Leu  Glu  Leu  Asp  Gly  Ile  Ile
                      165                      170                      175
Tyr  Leu  Gln  Ala  Thr  Pro  Glu  Thr  Cys  Leu  His  Arg  Ile  Tyr  Leu  Arg
                 180                      185                      190
Gly  Arg  Asn  Glu  Glu  Gln  Gly  Ile  Pro  Leu  Glu  Tyr  Leu  Glu  Lys  Leu
             195                      200                  205
His  Tyr  Lys  His  Glu  Ser  Trp  Leu  Leu  His  Arg  Thr  Leu  Lys  Thr  Asn
     210                      215                  220
Phe  Asp  Tyr  Leu  Gln  Glu  Val  Pro  Ile  Leu  Thr  Leu  Asp  Val  Asn  Glu
225                      230                       235                      240
Asp  Phe  Lys  Asp  Lys  Tyr  Glu  Ser  Leu  Val  Glu  Lys  Val  Lys  Glu  Phe
                     245                      250                      255
Leu  Ser  Thr  Leu
                 260
```

( 2 ) INFORMATION FOR SEQ ID NO:9:

( i ) SEQUENCE CHARACTERISTICS:
        ( A ) LENGTH: 624 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1109676

( x i ) SEQUENCE DESCRIPTION: SEQ ID NO:9:

```
Met  Glu  Ile  Pro  Gly  Ser  Leu  Cys  Lys  Lys  Val  Lys  Leu  Ser  Asn  Asn
 1              5                   10                        15

Ala  Gln  Asn  Trp  Gly  Met  Gln  Arg  Ala  Thr  Asn  Val  Thr  Tyr  Gln  Ala
               20                   25                   30

His  His  Val  Ser  Arg  Asn  Lys  Arg  Gln  Val  Val  Gly  Thr  Arg  Gly
          35                   40                   45

Gly  Phe  Arg  Gly  Cys  Thr  Val  Trp  Leu  Thr  Gly  Leu  Ser  Gly  Ala  Gly
     50                   55                        60

Lys  Thr  Thr  Val  Ser  Met  Ala  Leu  Glu  Glu  Tyr  Leu  Val  Cys  His  Gly
 65                      70                   75                             80

Ile  Pro  Cys  Tyr  Thr  Leu  Asp  Gly  Asp  Asn  Ile  Arg  Gln  Gly  Leu  Asn
                    85                   90                        95

Lys  Asn  Leu  Gly  Phe  Ser  Pro  Glu  Asp  Arg  Glu  Glu  Asn  Val  Arg  Arg
               100                  105                       110

Ile  Ala  Glu  Val  Ala  Lys  Leu  Phe  Ala  Asp  Ala  Gly  Leu  Val  Cys  Ile
               115                  120                       125

Thr  Ser  Phe  Ile  Ser  Pro  Tyr  Thr  Gln  Asp  Arg  Asn  Asn  Ala  Arg  Gln
     130                  135                       140

Ile  His  Glu  Gly  Ala  Ser  Leu  Pro  Phe  Phe  Glu  Val  Phe  Val  Asp  Ala
 145                      150                  155                            160

Pro  Leu  His  Val  Cys  Glu  Gln  Arg  Asp  Val  Lys  Gly  Leu  Tyr  Lys  Lys
                    165                       170                  175

Ala  Arg  Ala  Gly  Glu  Ile  Lys  Gly  Phe  Thr  Gly  Ile  Asp  Ser  Glu  Tyr
               180                  185                       190

Glu  Lys  Pro  Glu  Ala  Pro  Glu  Leu  Val  Leu  Lys  Thr  Asp  Ser  Cys  Asp
          195                       200                  205

Val  Asn  Asp  Cys  Val  Gln  Val  Val  Glu  Leu  Leu  Gln  Glu  Arg  Asp
     210                       215                       220

Ile  Val  Pro  Val  Asp  Ala  Ser  Tyr  Glu  Val  Lys  Glu  Leu  Tyr  Val  Pro
 225                      230                  235                            240

Glu  Asn  Lys  Leu  His  Leu  Ala  Lys  Thr  Asp  Ala  Glu  Ala  Leu  Pro  Ala
                    245                       250                       255

Leu  Lys  Ile  Asn  Lys  Val  Asp  Met  Gln  Trp  Val  Gln  Val  Leu  Ala  Glu
               260                       265                       270

Gly  Trp  Ala  Thr  Pro  Leu  Asn  Gly  Phe  Met  Arg  Glu  Arg  Glu  Tyr  Leu
          275                       280                  285

Gln  Cys  Leu  His  Phe  Asp  Cys  Leu  Leu  Asp  Gly  Gly  Val  Ile  Asn  Leu
     290                       295                       300

Ser  Val  Pro  Ile  Val  Leu  Thr  Ala  Thr  His  Glu  Asp  Lys  Glu  Arg  Leu
 305                      310                       315                       320

Asp  Gly  Cys  Thr  Ala  Phe  Ala  Leu  Val  Tyr  Glu  Gly  Arg  Arg  Val  Ala
               325                       330                       335

Ile  Leu  Arg  Asn  Pro  Glu  Phe  Phe  Glu  His  Arg  Lys  Glu  Glu  Arg  Cys
               340                       345                       350

Ala  Arg  Gln  Trp  Gly  Thr  Thr  Cys  Lys  Asn  His  Pro  Tyr  Ile  Lys  Met
          355                       360                       365

Val  Leu  Glu  Gln  Gly  Asp  Trp  Leu  Ile  Gly  Gly  Asp  Leu  Gln  Val  Leu
          370                       375                       380

Asp  Arg  Ile  Tyr  Trp  Asn  Asp  Gly  Leu  Asp  Gln  Tyr  Arg  Leu  Thr  Pro
 385                      390                       395                       400

Thr  Glu  Leu  Lys  Gln  Lys  Phe  Lys  Asp  Met  Asn  Ala  Asp  Ala  Val  Phe
                    405                       410                       415

Ala  Phe  Gln  Leu  Arg  Asn  Pro  Val  His  Asn  Gly  His  Ala  Leu  Leu  Met
                    420                       425                       430
```

| Gln | Asp | Thr 435 | His | Lys | Gln | Leu 440 | Leu | Glu | Arg | Gly | Tyr 445 | Arg | Arg | Pro | Val |
|---|---|---|---|---|---|---|---|---|---|---|---|---|---|---|---|
| Leu | Leu | Leu 450 | His | Pro | Leu | Gly 455 | Gly | Trp | Thr | Lys | Asp 460 | Asp | Asp | Val | Pro |
| Leu 465 | Met | Trp | Arg | Met | Lys 470 | Gln | His | Ala | Ala | Val 475 | Leu | Glu | Glu | Gly | Ile 480 |
| Leu | Asp | Pro | Glu | Thr 485 | Thr | Val | Val | Ala | Ile 490 | Phe | Pro | Ser | Pro | Met 495 | Met |
| Tyr | Ala | Gly | Pro 500 | Thr | Glu | Val | Gln | Trp 505 | His | Cys | Arg | Ala | Arg 510 | Met | Val |
| Ala | Gly | Ala 515 | Asn | Phe | Tyr | Ile | Val 520 | Gly | Arg | Asp | Pro | Ala 525 | Gly | Met | Pro |
| His | Pro 530 | Glu | Thr | Gly | Lys | Asp 535 | Leu | Tyr | Glu | Pro | Thr 540 | His | Gly | Ala | Lys |
| Val 545 | Leu | Thr | Met | Ala | Pro 550 | Gly | Leu | Ile | Thr | Leu 555 | Glu | Ile | Val | Pro | Phe 560 |
| Arg | Val | Ala | Ala | Tyr 565 | Asn | Lys | Lys | Lys | Arg 570 | Met | Asp | Tyr | Tyr 575 | Asp |
| Ser | Glu | His | His 580 | Glu | Asp | Phe | Glu | Phe 585 | Ile | Ser | Gly | Thr | Arg 590 | Met | Arg |
| Lys | Leu | Ala 595 | Arg | Glu | Gly | Gln | Lys 600 | Pro | Pro | Glu | Gly | Phe 605 | Met | Ala | Pro |
| Lys | Ala 610 | Trp | Thr | Val | Leu | Val 615 | Glu | Tyr | Tyr | Lys | Ser 620 | Leu | Glu | Lys | Ala |

(2) INFORMATION FOR SEQ ID NO:10:

(i) SEQUENCE CHARACTERISTICS:
        (A) LENGTH: 610 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 705385

(xi) SEQUENCE DESCRIPTION: SEQ ID NO:10:

| Met 1 | Ala | Phe | Leu | Pro 5 | Asn | Gly | Gln | Leu | Ala 10 | Thr | Asn | Val | Thr | Phe 15 | Gln |
|---|---|---|---|---|---|---|---|---|---|---|---|---|---|---|---|
| Thr | Gln | His | Val 20 | Ser | Arg | Ala | Lys | Arg 25 | Gly | Gln | Val | Leu | Gly 30 | Gln | Arg |
| Gly | Gly | Phe 35 | Arg | Gly | Cys | Thr | Val 40 | Trp | Phe | Thr | Gly | Leu 45 | Ser | Gly | Ala |
| Gly | Lys 50 | Thr | Thr | Ile | Ser | Phe 55 | Ala | Leu | Glu | Glu | Tyr 60 | Leu | Val | Ser | Gln |
| Gly 65 | Ile | Pro | Thr | Tyr | Ser 70 | Leu | Asp | Gly | Asp | Asn 75 | Val | Arg | His | Gly | Leu 80 |
| Asn | Lys | Asn | Leu | Gly 85 | Phe | Thr | Gln | Glu | Asp 90 | Arg | Glu | Glu | Asn | Ile 95 | Arg |
| Arg | Ile | Ser | Glu 100 | Val | Ala | Lys | Leu | Phe 105 | Ala | Asp | Gly | Gly | Ile 110 | Val | Cys |
| Leu | Thr | Ser 115 | Phe | Ile | Ser | Pro | Phe 120 | Lys | Arg | Asp | Arg | Asp 125 | Leu | Ala | Arg |
| Ser | Leu | His 130 | Glu | Gln | Ala | Gly | Leu 135 | Pro | Phe | Phe | Glu | Cys 140 | Phe | Val | Asp |
| Thr | Pro | Leu | Asp | Val | Cys | Glu | Gln | Arg | Asp | Val | Lys | Gly | Leu | Tyr | Lys |

-continued

```
              145                     150                     155                     160
Lys  Ala  Arg  Ala  Gly  Gln  Ile  Lys  Gly  Phe  Thr  Gly  Ile  Asp  Gln  Gln
                         165                     170                     175

Tyr  Glu  Ser  Pro  Asp  Ala  Pro  Glu  Ile  Gln  Leu  Tyr  Ala  Gly  Asn  Lys
                    180                     185                     190

Ser  Ile  Asp  Glu  Cys  Val  Gln  Glu  Val  Val  Ser  Leu  Leu  Gln  Lys  Asn
               195                     200                     205

Gly  Val  Val  Pro  Glu  Ser  Ala  Val  Asn  Ile  Val  Lys  Glu  Leu  Phe  Val
          210                     215                     220

Pro  Glu  Ser  Gly  Leu  Glu  His  Ala  Lys  Ala  Glu  Ile  Val  Asp  Leu  Pro
225                     230                     235                     240

Thr  Met  Glu  Ile  Thr  Lys  Leu  Asp  Thr  Gln  Trp  Val  Gln  Val  Leu  Ser
                    245                     250                     255

Glu  Gly  Trp  Ala  Thr  Pro  Leu  Thr  Gly  Phe  Met  Arg  Glu  Arg  Glu  Tyr
               260                     265                     270

Leu  Gln  Ser  Gln  His  Phe  Gly  Cys  Leu  Leu  Asp  Gly  Gly  Val  Thr  Asn
          275                     280                     285

Gln  Ser  Ile  Pro  Ile  Val  Leu  Pro  Val  His  Thr  Ala  Asp  Lys  Asp  Arg
     290                     295                     300

Leu  Glu  Gly  Ser  Ser  Ala  Phe  Ala  Leu  Ser  Tyr  Glu  Gly  Lys  Arg  Ile
305                     310                     315                     320

Ala  Ile  Leu  Arg  Thr  Pro  Glu  Phe  Tyr  Glu  His  Arg  Lys  Glu  Glu  Arg
                    325                     330                     335

Cys  Ser  Arg  Gln  Phe  Gly  Thr  Ser  Asn  Ala  Gly  Gln  Pro  Tyr  Val  Lys
               340                     345                     350

Met  Ile  Met  Glu  Ser  Gly  Asp  Trp  Leu  Val  Gly  Gly  Asp  Leu  Glu  Val
          355                     360                     365

Leu  Glu  Arg  Ile  Thr  Trp  Asn  Asp  Gly  Leu  Asp  Glu  Tyr  Arg  Leu  Thr
370                     375                     380

Pro  Asn  Glu  Leu  Arg  Ala  Lys  Phe  Arg  Ala  Leu  Asn  Ala  Asp  Ala  Val
385                     390                     395                     400

Phe  Ala  Phe  Gln  Leu  Arg  Asn  Pro  Val  His  Asn  Gly  His  Ala  Leu  Leu
                    405                     410                     415

Met  Thr  Asp  Thr  Arg  Arg  Arg  Leu  Thr  Glu  Arg  Gly  Tyr  Lys  Lys  Pro
               420                     425                     430

Val  Leu  Leu  Leu  His  Pro  Leu  Gly  Gly  Trp  Thr  Lys  Asp  Asp  Asp  Val
          435                     440                     445

Pro  Leu  Ala  Trp  Arg  Met  Lys  Gln  His  Gln  Ala  Ile  Leu  Asp  Glu  Lys
     450                     455                     460

Val  Leu  Asp  Pro  Asp  Tyr  Thr  Val  Met  Ala  Ile  Phe  Pro  Ser  Pro  Met
465                     470                     475                     480

Met  Tyr  Ala  Gly  Pro  Thr  Glu  Val  Gln  Trp  His  Ala  Lys  Ala  Arg  Met
                    485                     490                     495

Ser  Thr  Gly  Ala  Asn  Phe  Tyr  Ile  Val  Gly  Arg  Asp  Pro  Ala  Gly  Met
               500                     505                     510

Pro  His  Pro  Glu  Thr  Lys  Gln  Asp  Leu  Tyr  Asn  Ala  Thr  His  Gly  Ala
          515                     520                     525

Lys  Val  Leu  Thr  Met  Ala  Pro  Gly  Leu  Thr  Gln  Leu  Glu  Ile  Val  Pro
     530                     535                     540

Phe  Arg  Val  Ala  Ala  Tyr  Asn  Lys  Thr  Lys  Ser  Ala  Met  Asp  Phe  Tyr
545                     550                     555                     560

Asp  Pro  Glu  Arg  His  Asp  Glu  Phe  Met  Phe  Ile  Ser  Gly  Thr  Lys  Met
                    565                     570                     575
```

Arg Gly Met Ala Arg Ala Gly Glu Thr Pro Pro Asn Gly Phe Met Ala
            580                     585                     590

Pro Ser Ala Trp Lys Ile Met Val Glu Tyr Tyr Lys Thr Lys Ala Gln
            595                     600                     605

Gln Ser
610

( 2 ) INFORMATION FOR SEQ ID NO:11:

( i ) SEQUENCE CHARACTERISTICS:
          ( A ) LENGTH: 194 amino acids
          ( B ) TYPE: amino acid
          ( C ) STRANDEDNESS: single
          ( D ) TOPOLOGY: linear ( x i ) SEQUENCE DESCRIPTION: SEQ ID NO:11:

Met Glu Glu Lys Leu Lys Lys Thr Lys Ile Ile Phe Val Val Gly Gly
 1                5                  10                      15

Pro Gly Ser Gly Lys Gly Thr Gln Cys Glu Lys Ile Val Gln Lys Tyr
                20                  25                      30

Gly Tyr Thr His Leu Ser Thr Gly Asp Leu Leu Arg Ser Glu Val Ser
            35                  40                  45

Ser Gly Ser Ala Arg Gly Lys Lys Leu Ser Glu Ile Met Glu Lys Gly
    50                  55                  60

Gln Leu Val Pro Leu Glu Thr Val Leu Asp Met Leu Arg Asp Ala Met
65                  70                  75                  80

Val Ala Lys Val Asn Thr Ser Lys Gly Phe Leu Ile Asp Gly Tyr Pro
                85                  90                  95

Arg Glu Val Gln Gln Gly Glu Glu Phe Glu Arg Arg Ile Gly Gln Pro
                100                 105                 110

Thr Leu Leu Leu Tyr Val Asp Ala Gly Pro Glu Thr Met Thr Gln Arg
            115                 120                 125

Leu Leu Lys Arg Gly Glu Thr Ser Gly Arg Val Asp Asp Asn Glu Glu
        130                 135                 140

Thr Ile Lys Lys Arg Leu Glu Thr Tyr Tyr Lys Ala Thr Glu Pro Val
145                 150                 155                 160

Ile Ala Phe Tyr Glu Lys Arg Gly Ile Val Arg Lys Val Asn Ala Glu
                165                 170                 175

Gly Ser Val Asp Ser Val Phe Ser Gln Val Cys Thr His Leu Asp Ala
            180                 185                 190

Leu Lys ( 2 ) INFORMATION FOR SEQ ID NO:12:

( i ) SEQUENCE CHARACTERISTICS:
          ( A ) LENGTH: 194 amino acids
          ( B ) TYPE: amino acid
          ( C ) STRANDEDNESS: single
          ( D ) TOPOLOGY: linear ( x i ) SEQUENCE DESCRIPTION: SEQ ID NO:12:

Met Ser Thr Glu Lys Leu Lys His His Lys Ile Ile Phe Val Val Gly
 1                5                  10                      15

Gly Pro Gly Ser Gly Lys Gly Thr Gln Cys Glu Lys Ile Val His Lys
                20                  25                      30

Tyr Gly Tyr Thr His Leu Ser Thr Gly Asp Leu Leu Arg Ala Glu Val
            35                  40                  45

Ser Ser Gly Ser Glu Arg Gly Lys Lys Leu Gln Ala Ile Met Glu Lys
    50                  55                  60

-continued

| | | | | | | | | | | | | | | | |
|---|---|---|---|---|---|---|---|---|---|---|---|---|---|---|---|
| Gly 65 | Glu | Leu | Val | Pro | Leu 70 | Asp | Thr | Val | Leu | Asp 75 | Met | Leu | Arg | Asp | Ala 80 |
| Met | Leu | Ala | Lys | Ala 85 | Asp | Thr | Ser | Lys | Gly 90 | Phe | Leu | Ile | Asp | Gly 95 | Tyr |
| Pro | Arg | Glu | Val 100 | Lys | Gln | Gly | Glu | Glu 105 | Phe | Glu | Lys | Lys | Ile 110 | Ala | Pro |
| Pro | Thr | Leu 115 | Leu | Leu | Tyr | Val | Asp 120 | Ala | Gly | Lys | Glu | Thr 125 | Met | Val | Lys |
| Arg | Leu 130 | Leu | Lys | Arg | Gly | Glu 135 | Thr | Ser | Gly | Arg | Val 140 | Asp | Asp | Asn | Glu |
| Glu 145 | Thr | Ile | Lys | Lys | Arg 150 | Leu | Glu | Thr | Tyr | Tyr 155 | Lys | Ala | Thr | Glu | Pro 160 |
| Val | Ile | Ala | Phe | Tyr 165 | Lys | Gly | Arg | Gly | Ile 170 | Val | Arg | Gln | Leu | Asn 175 | Ala |
| Glu | Gly | Thr | Val 180 | Asp | Glu | Val | Phe | Gln 185 | Gln | Val | Cys | Ser | Tyr 190 | Leu | Asp |
| Lys | Leu | | | | | | | | | | | | | | |